(12) United States Patent
Shah et al.

(10) Patent No.: US 7,654,130 B2
(45) Date of Patent: Feb. 2, 2010

(54) GAS CHROMATOGRAPHY SYSTEM ARCHITECTURE INCORPORATING INTEGRATED THERMAL MANAGEMENT

(75) Inventors: Jagdish Shah, Southington, CT (US); Hua Chen, Ridgefield, CT (US); Shigeo Daito, Lexington, MA (US); Neil William Bostrom, Cambridge, MA (US)

(73) Assignee: Schlumberger Technology Corporation, Cambridge, MA (US)

( * ) Notice: Subject to any disclaimer, the term of this patent is extended or adjusted under 35 U.S.C. 154(b) by 66 days.

(21) Appl. No.: 11/614,735

(22) Filed: Dec. 21, 2006

(65) Prior Publication Data

US 2008/0121017 A1      May 29, 2008

Related U.S. Application Data

(63) Continuation-in-part of application No. 11/564,430, filed on Nov. 29, 2006.

(51) Int. Cl.
*G01N 30/04* (2006.01)
(52) U.S. Cl. .................................. 73/23.42; 73/23.35
(58) Field of Classification Search ............ 73/23.35, 73/23.39, 23.41, 23.42
See application file for complete search history.

(56) References Cited

U.S. PATENT DOCUMENTS

| 3,538,744 | A | * | 11/1970 | Karasek ..................... 73/23.39 |
| 4,350,586 | A | * | 9/1982 | Conlon et al. ............... 210/149 |
| 6,074,461 | A | * | 6/2000 | Wilson ....................... 96/102 |
| 6,607,580 | B1 | * | 8/2003 | Hastings et al. ................ 95/87 |
| 2004/0255643 | A1 | * | 12/2004 | Wise et al. ................. 73/23.39 |
| 2005/0223775 | A1 | * | 10/2005 | Klee et al. ................. 73/23.41 |

* cited by examiner

*Primary Examiner*—Daniel S Larkin
(74) *Attorney, Agent, or Firm*—James M. McAleenan; Jody Lynn DeStefanis; Dale Gaudier

(57) ABSTRACT

A self-contained micro-scale gas chromatography system that includes a plurality of gas chromatography components arranged on a micro-fluidic platform with nearly zero dead volume "tubeless" fluidic connections for the gas chromatography components. The micro-fluidic platform includes a plurality of flow channels that provide fluid flow paths for a sample, carrier gas and waste gas through and among the micro-fluidic platform and the plurality of gas chromatography components. The gas chromatography components may include a micro-scale gas chromatography column that is implemented as a MEMS device and includes embedded heating and cooling elements. The system may also include an on-board supply of carrier gas and on-board waste management, as well as a thermal management scheme making the system suitable for use in oil and gas wells and also other remote environments.

19 Claims, 21 Drawing Sheets

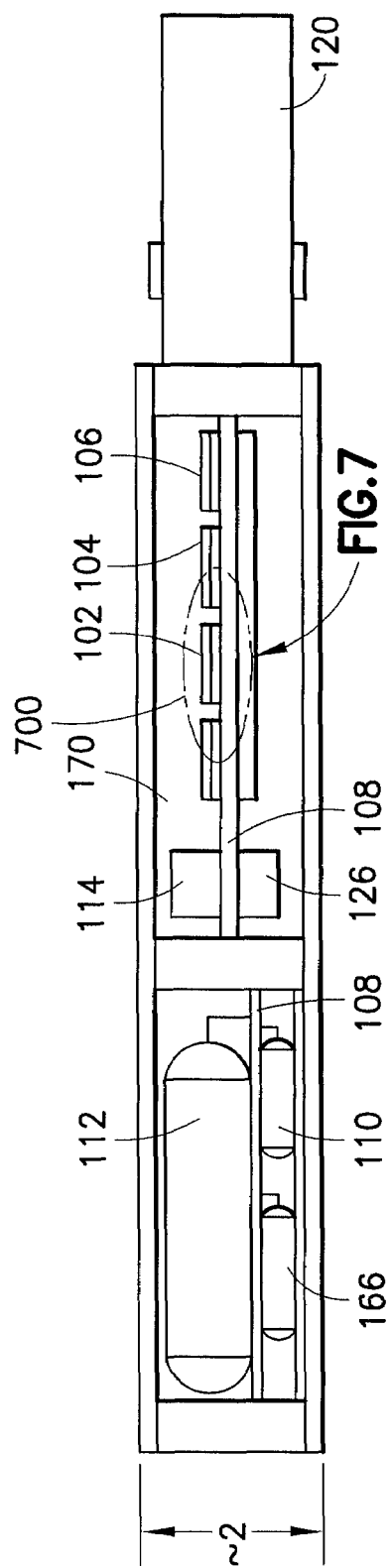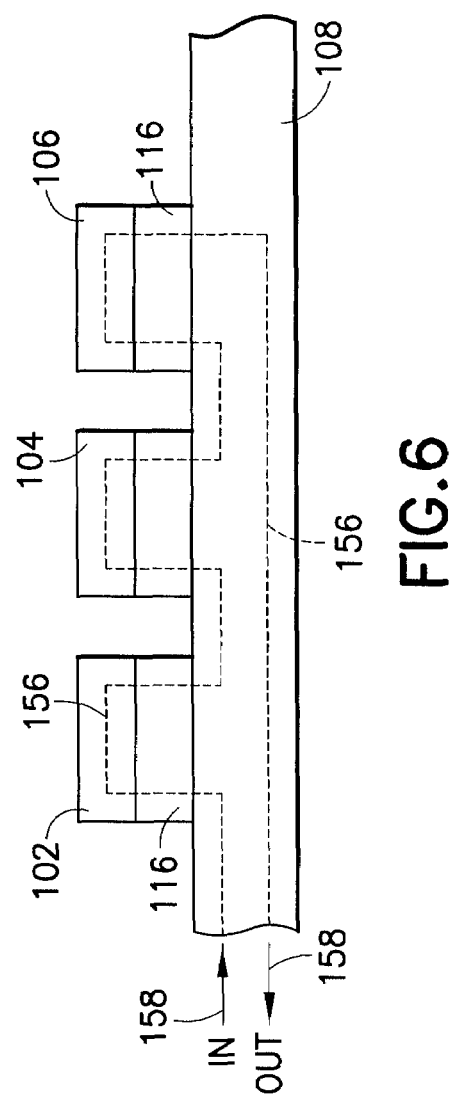

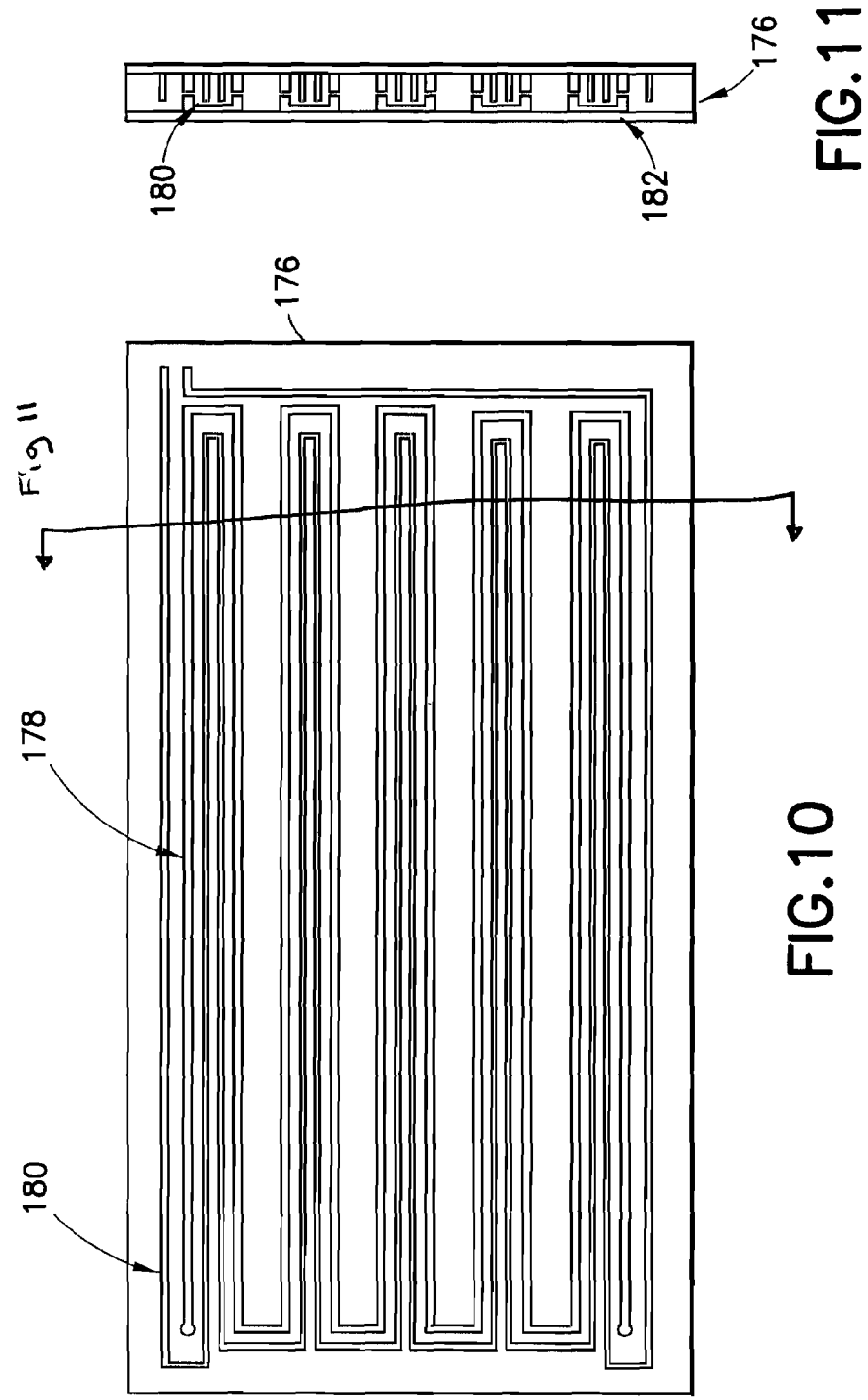

GAS CHROMATOGRAPHY SYSTEM ARCHITECTURE INCORPORATING INTEGRATED THERMAL MANAGEMENT

CROSS REFERENCE TO RELATED APPLICATIONS

This application is a continuation-in-part of, and claims priority under 35 U.S.C. § 120 to, co-pending U.S. application Ser. No. 11/564,430 entitled "GAS CHROMATOGRAPHY SYSTEM ARCHITECTURE" filed Nov. 29, 2006, which is herein incorporated by reference in its entirety.

BACKGROUND

1. Field of Invention

The present invention relates to gas chromatography systems and, more particularly, to small-scale systems that may be suitable for operation in various environments.

2. Discussion of Related Art

Gas chromatography uses chromatographic columns to separate molecular species within a sample fluid and thereby to extract information about the sample fluid. A chromatographic column has a stationary phase fixed inside the column and a mobile phase which is a carrier gas such as helium that flows through the column. The sample is collected, injected into the column and then transported by the carrier gas into and through the column. If the sample is in a liquid state, the sample may first be injected into a vaporization chamber to be vaporized then transported through the column. As a sample progresses through the column, the individual molecular components are slowed down based on their affinity to the stationary phase. At the outlet of the column, a detector measures the quantity of each component as it exits the column. The calibrated retention time, i.e., the time a component spends in the column, identifies the component.

Conventional gas chromatography apparatus is built around a standard chromatographic column and injector which, when packaged with thermal management apparatus, becomes bulky. The larger the column and flow channels, the greater the rate of carrier gas consumption. As a result, for conventional systems, a relatively large supply of carrier gas is needed. Typically, chromatographic analysis of a sample using a traditional system is done in a laboratory or other environment where a large reservoir of carrier gas is present.

Boreholes are typically small diameter holes having a diameter of approximately five (5) inches or less, although open holes may have larger diameters. In addition, vibrations and typically high temperature (about 200 degrees Celsius) and high pressure environments are experienced down-hole, adding further constraints to the design of a system suitable for down-hole operation. Furthermore, the temperature of components of a chromatogram should be controlled and monitored accurately, which is difficult in a down-hole environment. Thus, given the space and other constraints of down-hole environments, the use of traditional gas chromatography devices down-hole would be challenging.

There have been some attempts to develop smaller gas chromatography devices. For example various companies have introduced portable gas chromatography apparatus employing a limited micro-scale technology. However, none have been designed for down-hole applications. One such example system is that produced by SLS MICRO TECHNOLOGY GmbH. The SLS unit incorporates a micro-scale column and detector with a motorized sliding injector of about 1 inch by 1 inch and about 1.5 inches in length. However, the SLS device lacks the inclusion of high-pressure sampling and thermal management requirements to operate in a high temperature (e.g., about 200 C) down-hole environment. The SLS unit also lacks an on-board supply of carrier gas and means of waste disposal that would be desirable, or even necessary, for down-hole applications. Furthermore, the SLS system uses a glued component layout consisting of fused silica tubes to provide fluidic inter-connections which may not be suitable for high-temperature environments.

Another example is a system produced by the C2V (Concept to Volume) company based in the Netherlands. The C2V unit includes a micro-scale injector and detector. However, the unit uses traditional columns housed in a heated canister. The injector, although micro-scale, needs an external supply of regulated fluidic pressure to operate various micro-valves and is not designed to operate in a high temperature and pressure environment. The fluidic connections are achieved by glued capillary tubes which may be unsuitable for down-hole applications or other high temperature environments. In addition, the C2V unit does not include an on-board supply of carrier gas and waste disposal is not addressed. The flow rate requirements are much larger than the SLS device, and would require considerably larger volumes of carrier gas. The C2V device also does not have thermal management and operates in isothermal mode only, that is, all components are operated at same temperature. Neither the SLS device nor the C2V device has a tool architecture that is functionally suitable for down-hole applications.

SUMMARY OF INVENTION

Various aspects and embodiments of the invention are directed to a gas chromatography system that includes micro-scale components deployed in a manner suitable for down-hole conditions. In order to perform chromatographic analyses down-hole or in other non-laboratory environments such as, for example, underwater environments, other underground (i.e., non-borehole) locations or space-limited environments or non-Earth environments (e.g., in space or on other planets), the system may be self-contained, including an on-board supply of carrier gas and on-board waste disposal. Further, the small size of systems according to embodiments of the invention may provide critical advantages that improve operability and reliability of gas chromatographic analysis, particularly in down-hole environments. For example, the small size of embodiments of the system may facilitate thermal management, as discussed below.

According to one embodiment, a gas chromatography apparatus may comprise a micro-fluidic platform comprising a plurality of micro-channels disposed thereon, an injector coupled to the micro-fluidic platform and constructed and arranged to provide a sample for analysis, one or more gas chromatography columns coupled to the injector via the micro-fluidic platform and constructed and arranged to receive the sample from the injector and to produce an output dependent on a chemical composition of the sample. The apparatus may further comprise one or more detectors coupled to the gas chromatography column(s) and constructed and arranged to receive the output from the gas chromatography column(s), as well as a housing substantially surrounding and enclosing the micro-fluidic platform, the injector, the gas chromatography column(s) and the detector(s), wherein the plurality of micro-channels provide flow channels for the sample and the output from the gas chromatography column(s). In one example, at least one of the injector, the gas chromatography column(s) and the detector(s) is implemented at the micro-scale.

According to another embodiment, a micro-scale gas chromatography system may comprise a plurality of gas chromatography components, and a micro-fluidic platform coupled to the plurality of gas chromatography components to interconnect the plurality of gas chromatography components, wherein the micro-fluidic platform comprises a plurality of flow channels that provide fluid flow paths for a sample, carrier gas and waste gas through and among the micro-fluidic platform and the plurality of gas chromatography components. In one example, the plurality of gas chromatography components includes an injector, at least one gas chromatography column and at least one detector. The system may further comprise means for individually controlling operating temperatures of at least some of the plurality of gas chromatography components, including, for example, a heater disposed adjacent at least one of the injector, the gas chromatography column and the detector, and optionally thermal traps and thermal stops disposed about the plurality of gas chromatography components to thermally isolate the plurality of components from one another.

Another embodiment includes a micro-scale gas chromatography column which may comprise a substrate, at least one contiguous column channel formed in a first surface of the substrate, at least one contiguous heater channel formed in the first surface of the substrate, interleaved with the at least one column channel, and at least one contiguous cooling channel formed in a second surface of the substrate. In one example, the substrate may be a SILICON-glass substrate. The column may further include a stationary phase deposited on a surface of the at least one contiguous column channel. In one example, the micro-scale gas chromatography column may further comprise a resistive wire disposed in the at least one contiguous heater channel.

According to another embodiment, a gas chromatography apparatus may comprise a micro-scale gas chromatography column including a substrate having a column channel formed in a first surface of the substrate, the column channel having an inlet port and an outlet port, and a surface of the column channel being coated with a stationary phase, and a micro-fluidic platform coupled to the inlet port and to the outlet port of the column channel. In one example, the micro-scale gas chromatography column may further include a heater channel formed in the substrate. The apparatus may include an electrical power supply and a heating element disposed in the heater channel and coupled to the electrical power supply. The heating element may be, for example, a resistive wire or a conductive coating disposed on a surface of the heater channel. In one example, the heater channel may be formed in the first surface of the substrate, interleaved with the column channel. In this example, the column may further include at least one cooling channel formed in a second surface of the substrate, the second surface being opposite the first surface. The gas chromatography apparatus may further comprise a cooling system including a coolant, wherein the cooling system is coupled to the at least one cooling channel such that the coolant (e.g., a liquid) flows in the at least one cooling channel. In another example, heater channel may be formed in a second surface of the substrate, the second surface being opposite the first surface. In this example, the micro-scale gas chromatography column may further comprise at least one cooling channel formed in the first surface of the substrate. The micro-scale gas chromatography column may be anodically bonded to the micro-fluidic platform.

Another embodiment is directed to a method of manufacture of a micro-scale gas chromatography column. The method may comprise acts of defining a plurality of column channels on a SILICON-on-insulator (SOI) wafer, defining a plurality of cooling channels on the SOI wafer, defining a plurality of heater channels on the SOI wafer, rendering the wafer substantially chemically inactive, and dicing the wafer into a plurality of microchips, each microchip corresponding to a micro-scale gas chromatography column. In one example, the SOI wafer may comprise a SILICON layer, a SILICON substrate, and buried SILICON dioxide layer sandwiched between the SILICON layer and the SILICON substrate, and the acts of defining the plurality of column channels and defining the plurality of cooling channels may include forming the column channels and the cooling channels in the SILICON layer by deep reactive ion etching. In another example, the act of defining the plurality of heater channels may include forming the heater channels in the SILICON substrate by deep reactive ion etching. In one embodiment, the method may further comprise preparing a PYREX (generic name, borosilicate glass) cover layer and bonding the PYREX cover layer to a surface of the SILICON layer, such that the PYREX cover layer covers the plurality of column channels and the plurality of cooling channels. In another example, the each column channel of the plurality of column channels includes an inlet port and an outlet port, and preparing the PYREX cover layer may includes ultrasonically drilling fluid access holes through the PYREX cover layer. In this example, bonding the PYREX cover layer to the SILICON layer may include aligning the PYREX cover layer with the SILICON layer such that the fluid access holes align with the inlet ports and outlet ports of the plurality of column channels. In another example, the method may further comprise disposing a heating element in each heater channel of the plurality of heater channels. In a further example, the method may also comprise bonding a second PYREX cover layer to a surface of the SILICON substrate such that the second PYREX cover layer covers the plurality of heater channels.

BRIEF DESCRIPTION OF THE DRAWINGS

Various aspects and embodiments of the invention are described below with reference to the accompanying figures. In the drawings, which are not intended to be drawn to scale, each identical or nearly identical component that is illustrated in various figures is represented by a like numeral. For purposes of clarity, not every component may be labeled in every drawing. In the drawings:

FIG. 5 is a block diagram of another embodiment of a gas chromatography system according to the invention;

FIG. 6 is a block diagram illustrating a portion of a gas chromatography apparatus including fluidic channels, according to an embodiment of the invention;

FIG. 10 is a top view of a geometry of one embodiment of a gas chromatography column according to an embodiment of the invention;

FIG. 11 is a cross-sectional view of the gas chromatography column of FIG. 10 taken along line 11-11 in FIG. 10;

DETAILED DESCRIPTION

Figure 1:
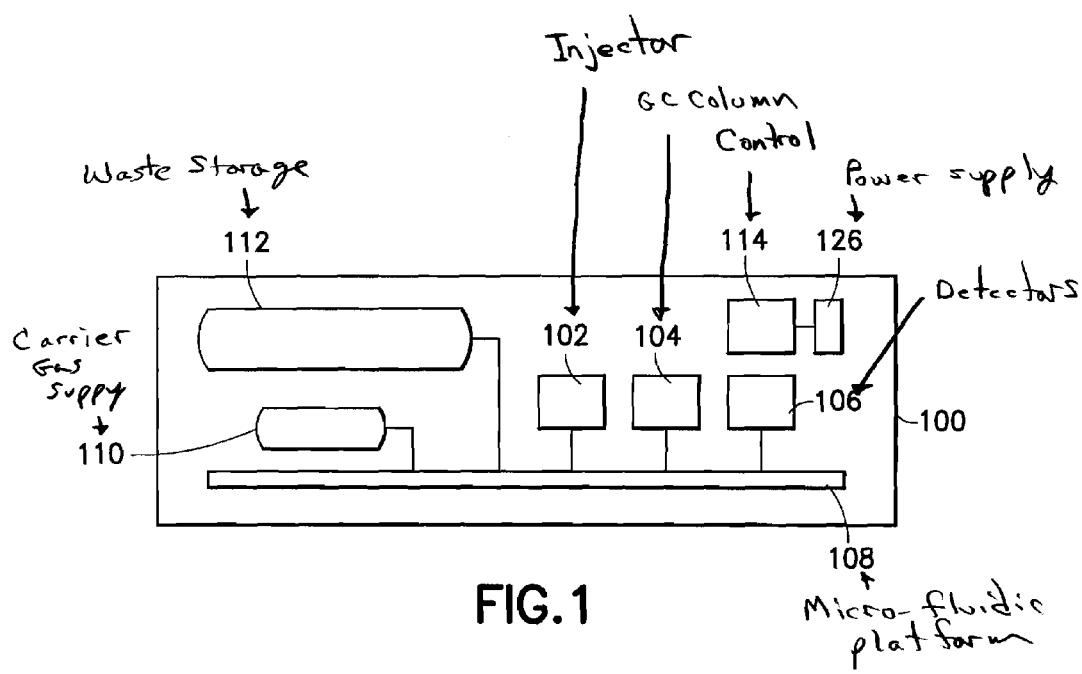
FIG. 1 is a block diagram illustrating one embodiment of a gas chromatography system according to the invention.

Embodiments of the invention and aspects thereof are directed to a gas chromatography apparatus and system that incorporates micro-scale components and may be suitable for use in a variety of environments. Traditionally, gas chromatographic analysis is performed on the surface of the earth, usually in a laboratory or similar environment. A sample may be collected at a remote location or sample site, for example, an underground or underwater location, and then returned to a testing facility, such as a laboratory, for chromatographic analysis. As discussed above, although there have been some developments of portable gas chromatography systems, none have been suitable for down-hole applications. Therefore, to address these and other limitations in the prior art, aspects and embodiments of the invention are directed to a gas chromatography system having an architecture that allows for down-hole operation. For example, boreholes are typically small diameter holes having a diameter of approximately five (5) inches or less. Therefore, according to one embodiment, a gas chromatography system that includes components arranged in a tubular housing, the housing having as small an outer diameter as feasible, may be well suited to down-hole applications. In addition, high temperature and high pressure are generally experienced in down-hole environments. Therefore, the components and/or housing of the apparatus should be able to accommodate these conditions. For example, in one embodiment, a gas chromatography apparatus may include techniques thermal management. In addition, a gas chromatography apparatus according to embodiments of the invention may be a self-contained unit including an on-board supply of carrier gas and on-board waste management. These and other features and aspects of embodiments gas chromatography apparatus according to embodiments of the invention are discussed in more detail below with reference to the accompanying figures.

It is to be appreciated that this invention is not limited in its application to the details of construction and the arrangement of components set forth in the following description or illustrated in the drawings. The invention is capable of other embodiments and of being practiced or of being carried out in various ways. For example, it is to be appreciated that the gas chromatography apparatus described herein is not limited to use in boreholes and may be used in a variety of environments and application such as, for example, other underground applications, underwater and/or space applications. Examples of specific implementations are provided herein for illustrative purposes only and are not intended to be limiting. In particular, acts, elements and features discussed in connection with one embodiment are not intended to be excluded from a similar role in other embodiments. Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

Referring to FIG. 1, there is illustrated a block diagram of one embodiment of a gas chromatography (GC) system according to the invention. The system may comprise a plurality of components contained within a housing 100. These components may include, for example, an injector 102, one or more gas chromatography columns 104 and one or more detectors 106. These components are collectively referred to as GC components and are described in more detail below. These components may be coupled to one another either directly or via a micro-fluidic platform 108 which is also discussed in detail below. In addition, the system may include a power supply 126 and control components 114. In one example, the power supply may include a wire line that may connect the gas chromatography system too an external source of power (e.g., a generator or public electricity supply). In another example, particularly where several of the GC components may be micro-scale components, the power requirements may be sufficiently to small to allow battery operation and the power supply 126 may thus include one or more batteries. These batteries may be, for example, Lithium Thionel Chloride batteries rated for high temperature environments. As discussed above, the system may also include a carrier gas supply 110 as well as a waste storage component 112. Having an on-board supply of carrier gas may allow the GC system to be operated down-hole (or in another remote environment) without requiring connection to an external supply of gas. In a down-hole or other pressurized environment (e.g., deep underwater locations), it may be difficult, if not impossible, to vent waste gas to outside of the gas chromatography system due to high ambient pressure. Therefore, the on-board waste storage component 112 may be particularly desirable. By making at least some of the system components micro-scale components, a chromatography device small enough to comply with the space constraints of down-hole environments may be realized.

It is to be appreciated that although embodiments of chromatography systems may be referred to herein as micro-scale systems, not all of the components are required to be micro-scale and at least some components may be meso-scale or larger. This is particularly the case where the device is intended for use in environments where the space constraints are not as tight as for down-hole applications. As used herein, the term "micro-scale" is intended to mean those structures or components having at least one relevant dimension that is in a range of a few micrometers to approximately one (1) millimeter (mm). In order to achieve these scales, manufacturing technologies such as SILICON micro-machining, chemical etching and other methods known to those skilled in the art may be used. Thus, for example, a "micro-scale" gas chromatography column may be constructed using a SILICON wafer into which are etched or machined very small channels of the micrometer-scale width. Although the overall size of such a column may be a few centimeters, (in width and/or length), a relevant feature, namely, the channels, are not only micro-scale, but also may be manufactured using micro-machining (or chemical etching) techniques. Therefore, such a column may be referred to as a micro-scale column. Such columns have very low mass when packaged and may therefore allow for easier thermal management compared to traditionally packaged columns. By contrast, "meso-scale" components of a gas chromatograph, e.g., a column, injector and/or detector, may have relevant dimensions that may be between several micrometers and a few millimeters and may be made using traditional manufacturing methods such as milling, grinding, glass and metal tube drawing etc. Such components tend to be bulkier than components that may be considered "micro-scale" components. Thus, for example, a traditional gas chromatography column may be made of a stainless steel or glass capillary tube having an inside diameter on the order of about one hundred (100) micrometers, but a length of several meters. A meso-scale injector, for example, may also be made using traditional manufacturing techniques and may measure a few tens of millimeters in size. Thus, the terms micro-scale and meso-scale relate not only to the size of relevant dimensions or parameters of components but also to the manufacturing techniques used to produce the components. As known to those skilled in the art, there are no defined boundaries between these terms and they do overlap. However, the distinction between micro-scale and meso-scale, as discussed above, refers to both the manufacturing technique and the length scale.

As discussed above, a gas chromatography apparatus according to embodiments of the invention may comprise an injector 102, at least one column 104 and at least one detector 106 interconnected via a micro-fluidic platform 108. The micro-fluidic platform may include flow channels that provide fluid connections between the various GC components, as discussed further below. It is to be appreciated that various embodiments of the apparatus may include one or more columns that may be disposed in a parallel or series configuration. In a parallel configuration, a sample may be directed into multiple columns at the same time using, for example, a valve mechanism that couples the columns to the micro-fluidic platform. The output of each column may be provided to one or more detectors. For example, the same detector may be used to analyze the output of multiple columns or, alternatively, some or all of the columns may be provided with a dedicated detector. In another example, multiple detectors may be used to analyze the output of one column. Multiple detectors and/or columns may be coupled together in series or parallel. In a series configuration of columns, the output of a first column may be directed to the input of a second column, rather than to waste. In one example, a detector may be also positioned between the two columns as well as at the output of the second column. In another example, a detector may be positioned only at the output of the last column of the series. It is to be appreciated that many configurations, series and parallel, are possible for multiple columns and detectors and that the invention is not limited to any particular configuration or to the examples discussed herein.

In one embodiment of a micro-scale gas chromatograph, some or all of the GC components may be MEMS (Micro-Electro-Mechanical Systems) devices. Such devices may be small and thus appropriate for a system designed to fit within a small housing 100 suitable for down-hole deployment. In addition, such devices may be easily coupled to the micro-fluidic platform 108. In one example, some or all of the three components may be MEMS devices that are approximately two (2) centimeters (cm) by two (2) cm by 1-2 mm thick. Arranged linearly, as shown, for example, in FIG. 1, these devices could be easily be housed within a cylinder having an inner diameter of about two (2) inches or less and a length of about four (4) inches. However, it is to be appreciated that the injector 102, column 104 and detector 106 need not be discrete devices and also need not be linearly arranged within the housing 100. Many other configurations are also possible and are considered included in this disclosure. In addition, many variations on the size and thickness of the devices are also possible and the invention is not limited to the specific example given herein.

Figure 2A:
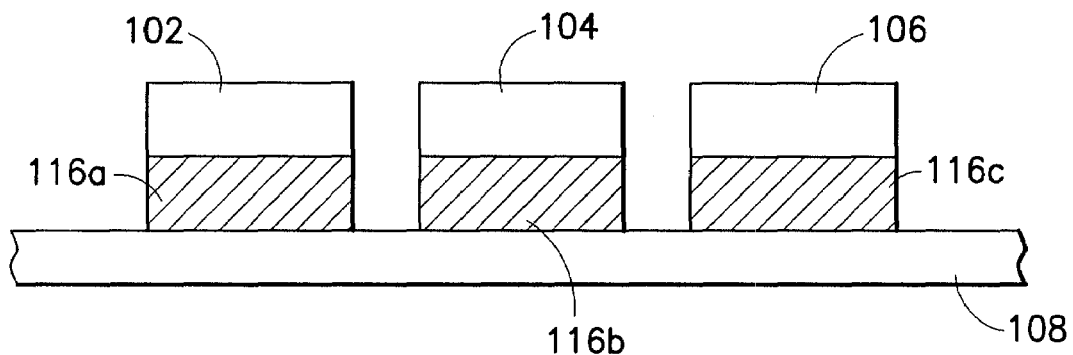
FIG. 2A is a block diagram of one example of component layout for a gas chromatography apparatus according to aspects of the invention.
Figure 2B:
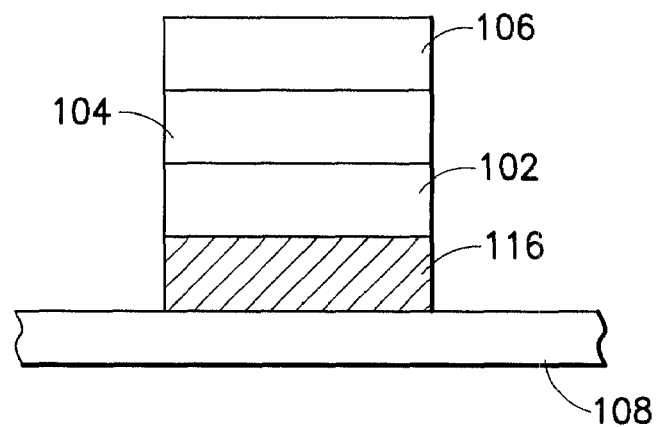
FIG. 2B is a block diagram of another example of component layout for a gas chromatography apparatus according to aspects of the invention.
Figure 2C:
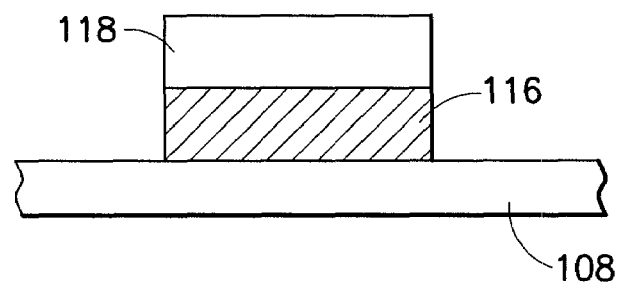
FIG. 2C is a block diagram of another example of component layout for a gas chromatography apparatus according to aspects of the invention.

For example, referring to FIGS. 2A-2C, there are illustrated three examples of arrangements of the injector 102, column 104 and detector 106. In FIG. 2A, the GC components are illustrated in a linear arrangement, similar to that shown in FIG. 1. Such a linear configuration may be advantageous when it is desirable to keep the inner diameter of the housing as small as possible and where the length of the housing is less critical. This configuration may also have the advantage of allowing each discrete device to have individual thermal management including, for example, individual heating devices 116a, 116b, and 116c, as shown. Therefore, this linear configuration may be preferred in application where the injector, column(s) and detector(s) are to be operated at different temperatures. In the illustrated example, the heating elements are shown positioned between the respective component and the micro-fluidic platform 108; however, it is to be appreciated that the invention is not limited to the illustrated arrangement. Referring to FIG. 2B, the injector 102, column 104 and detector 106 are illustrated in a stacked arrangement, one on top of the other. Such a stacked arrangement may be preferable if there is a need or desire to shorten the length of the housing. For example, the stacked components, along with other components making up the gas chromatograph, may fit within a housing having an inner diameter of less than about 2 inches and a length of about 1.5 inches. In another embodiment, illustrated in FIG. 2C, integrated MEMS device 118 may contain an injector, column and detector. In one example, such an integrated MEMS device may be less than about 2 cm by about 5 cm by about 1 to 2 mm in height. The stacked and integrated embodiments shown in FIGS. 2B and 2C may be particularly suitable for isothermal analysis where all active components are held at the same temperature. In these examples, one heater 116 may suffice for all of the injector, column and detector components.

According to one embodiment, a micro-scale chromatograph according to aspects of the invention may comprise one or more components at the micro-fluidic scale, wherein the flow channels are very small. For example, in one embodiment, the flow channels may be on the order of about sixty (60) microns. Volumetric flow rates of carrier gas through the flow channels scale approximately as the square of the effective diameter of the channel. Therefore, a micro-scale gas chromatography apparatus may inherently require a significantly smaller supply of carrier gas when compared to a meso-scale or larger scale system. In one example, a micro-scale gas chromatography apparatus may consume carrier gas at a rate five (5) or even ten (10) times slower than a traditional, larger gas chromatography system that includes much larger flow channels. This may be advantageous in that both the carrier gas supply 110 and waste storage component 112 (see FIG. 1) may be comparatively smaller as they may contain a smaller volume of gas. For example, assuming that the carrier gas consumption for a micro-scale gas chromatograph is on the order of about 100 microliters per minute (µL/min), for a 1000-minute service down-hole, one hundred (100) milliliters (mL) of carrier gas may be required. Assuming that the analysis is performed at near-atmospheric pressure (approximately 15 psi), a waste storage container 112 of about one hundred (100) mL would be needed. In one embodiment, the carrier gas supply may be stored in a high-pressure (e.g., about 1000 psi) container 110 and thus, the size of the container 110 may be extremely small.

Containers of these and similar sizes may easily fit within a housing 100 that is formed as a slender cylinder. For example, a cylindrical housing 100 that has an inner diameter of about two (2) inches or less and a length of about five (5) inches or less may contain the above-mentioned waste storage container 112, carrier gas supply container 110. In one example, the housing 100 may be a cylinder having an inner diameter of approximately 1.75 inches and a length of about five (5) inches. A housing of this or similar size may fit comfortable down an borehole or into another narrow opening, as discussed above. In one example, the gas chromatography analysis may be performed at higher than atmospheric pressure. In this case, the waste gas may be compressed, thus needing an even smaller waste container 112. Of course, it will be appreciated that the amount of carrier gas needed, and thus also the sizes of the carrier gas and waste storage containers, may vary depending on the actual flow rates in the system as well as the desired length of service time. Accordingly, the invention is not limited to the specifics of the examples discussed herein which are given for the purpose of illustration and are not intended to be limiting.

Figure 3:
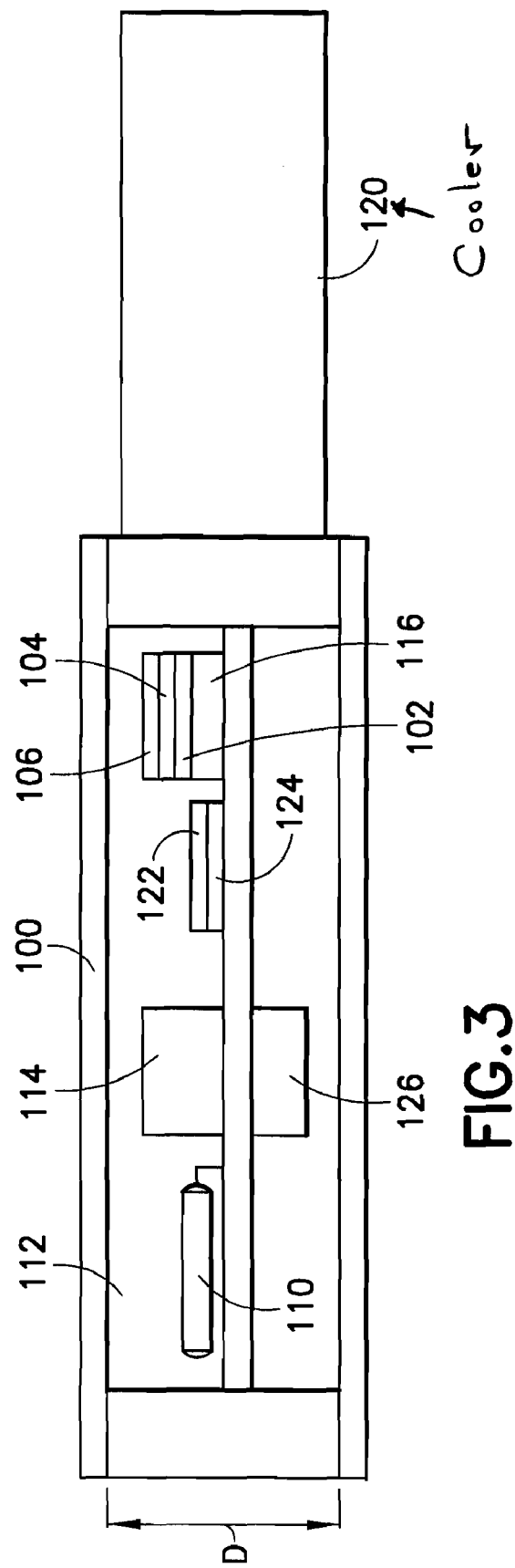
FIG. 3 is a block diagram of another embodiment of a gas chromatography system according to the invention.

Referring to FIG. 3, there is illustrated a block diagram of another embodiment of a gas chromatography apparatus according to the invention. In this embodiment, the injector 102, column 104 and detector 106 are shown in a stacked arrangement, one on top of the other. However, it is to be appreciated than any of the above-mentioned configurations may be used. Also shown are some thermal management components including the heater(s) 116 discussed above and a cooler 120. These components are discussed in more detail below. In the illustrated embodiment, the housing 100 that contains the GC components, the micro-fluidic platform 108, carrier gas container 110 and other components, may also serve as the waste storage container 112. This may eliminate the need for a separate waste storage container which may reduce the overall size of the system. In one example of this embodiment, the housing 100 may be a cylinder that has an inner diameter D of about two (2) inches and a length of about eight (8) inches.

According to some embodiments of the invention, a gas chromatography system may also include a sampler 122. Before a fluid to be analyzed (referred to herein as a "formation fluid") can be introduced into the gas chromatography apparatus, a sample of the formation fluid may be extracted from its environment (e.g., from a rock formation in the case of boreholes). Thus, a self-contained gas chromatography system may include the sampler 122 to perform this extraction/sampling. In down-hole environments, the formation fluid may be at high pressure (e.g., about 20 Kpsi) and high temperature (up to about 200 C or even higher). Traditional chromatographic methods require that the sample be de-pressurized, while carefully modulating its temperature to control the separation process. According to one embodiment, a micro-scale sampler can be may be integrated into the gas chromatography apparatus. The sampler 122 may be coupled to a heater 124 to achieve at least some temperature modulation. In one example, the sampler 122 may be a multi-stage sampler and phase separator. In this example, the sampler 122 may perform phase separation to eliminate water, which can deteriorate gas chromatographic analysis. Being at the microscale, the sampler may then isolate a minute quantity of formation fluid, for example, in the sub-micro liter or nanoliter range. Depressurization may be accomplished in an expansion chamber accompanied by appropriate temperature control to preserve the sample elution.

Figure 4A:
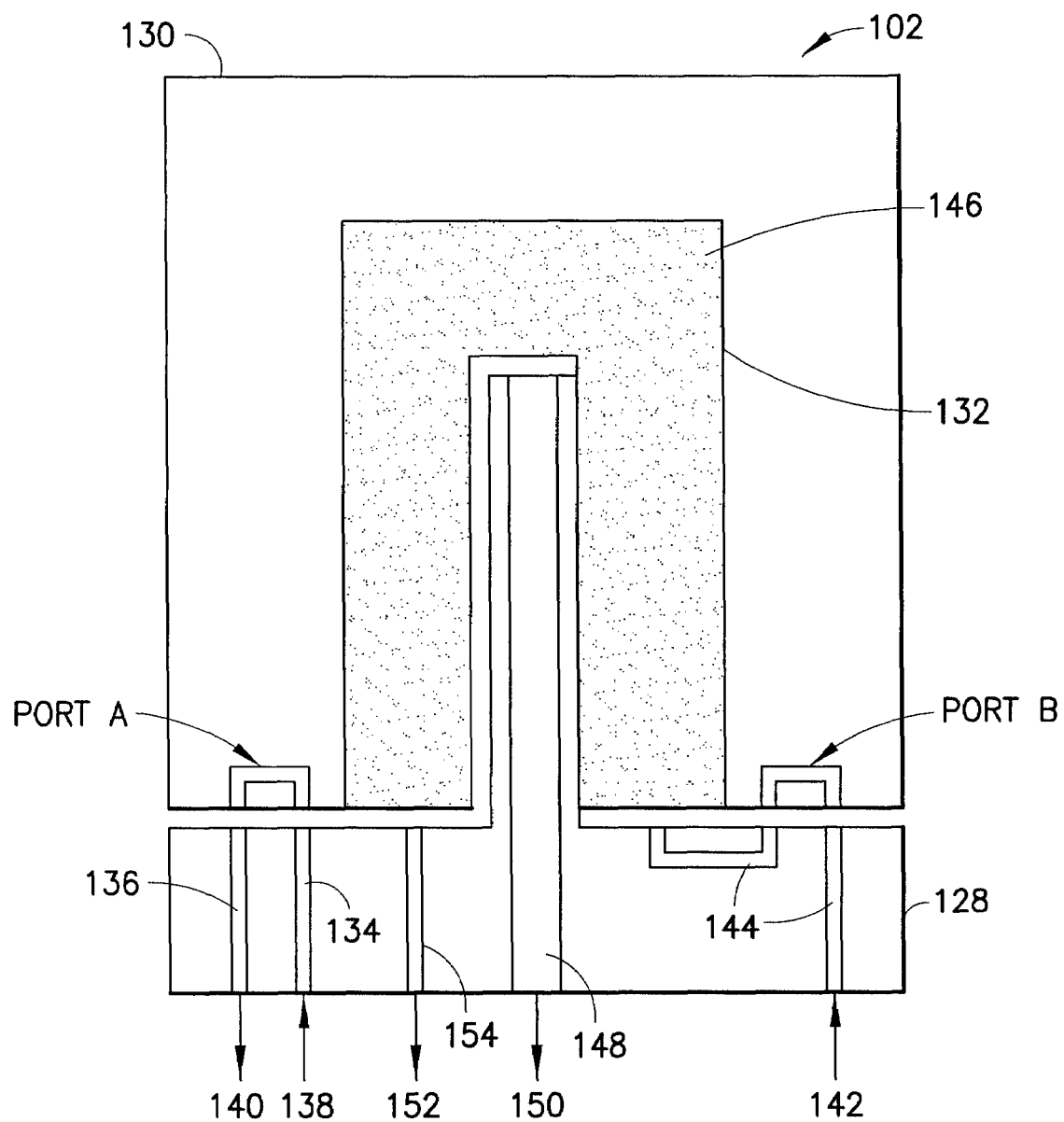
FIG. 4A is a diagram of one embodiment of an injector according to the invention.

According to one embodiment, depressurization may be accomplished by the injector 102. Referring to FIG. 4A, there is illustrated one example of an injector 102 according to an embodiment of the invention. The injector may be implemented at the micro-scale, but may also be a meso-scale or larger device. The injector 102 may comprise a stator 128 that is coupled to the sampler 122 (not shown) and to the micro-fluidic platform (not shown), and a rotor 130 coupled to the stator. The injector also comprises an expansion chamber 132. As discussed above, the sampler may collect a small sample of formation fluid and, in at least some embodiments, may separate water out from the sample of formation fluid. The remaining high pressure sample, indicated by arrow 138, may be supplied from the sampler through a flow channel 134 to Port A of the injector. When the injector is in a sampling state (shown in FIG. 4A), the sample may flow through Port A and back out of the injector via flow channel 136, indicated by arrow 140. Meanwhile, at Port B, carrier gas at low-pressure (indicated by arrow 142) may continuously flows into the vaporization chamber 132 via flow channel 144 and Port B.

Figure 4B:
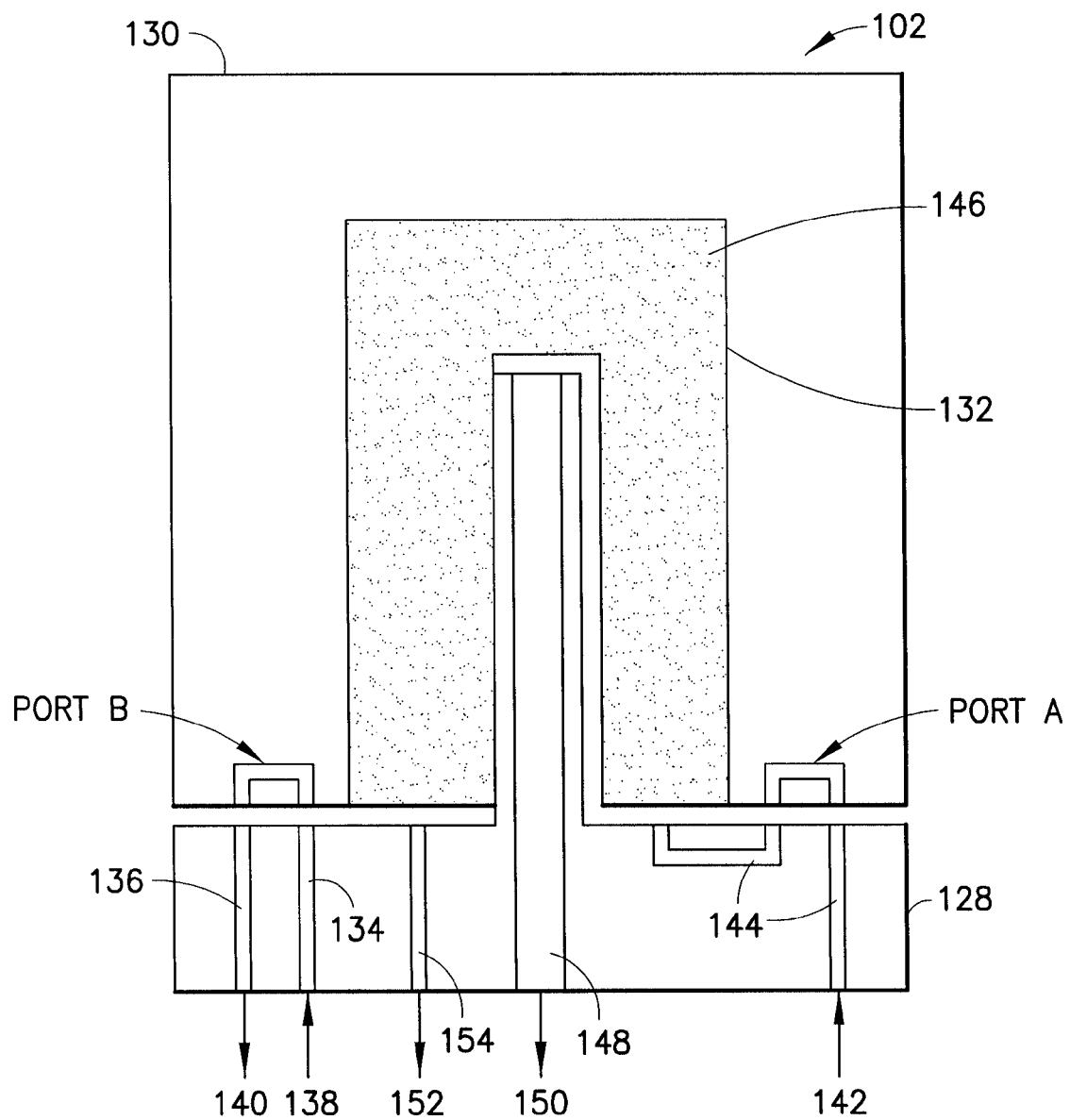
FIG. 4B is a diagram of the injector of FIG. 4A shown in an alternate state.

To inject a sample of formation fluid into the gas chromatography apparatus, the rotor may be turned by an external device (not shown) causing Port A to line up with flow channel 144 and Port B to line up with flow channels 134 and 136, as shown in FIG. 4B. The sample of formation fluid trapped in Port A may be flushed into the heated vaporization chamber 132 by the low-pressure carrier gas indicated by arrow 142. In one embodiment, the vaporization chamber 132 may be filled with a heated distribution material 146 such as, for example, silica glass wool. The distribution material 146 may provide a large surface area for sample vaporization and may disperse the injected sample in the flow of carrier gas. The high surface area distribution material may also trap any non-vaporized components, such as asphaltenes and sand which may be found in down-hole formation fluids, preventing these components from entering the column. A portion of the vaporized sample (indicated by arrow 150) may be forced into the column (not shown) via flow channel 148. The remaining vaporized sample and carrier gas (indicated by arrow 152) is waste and may exit the injector 102 via flow channel 154 to the waste storage container (not shown). The injector may thus provide a split injection scheme. The rotor may then be rotated back to the original position (illustrated in FIG. 4A) to collect a new sample of formation fluid at Port A.

According to one embodiment, a gas chromatography system may provide for in situ calibration of the gas chromatography apparatus. Referring to FIG. 5, there is illustrated another embodiment of a gas chromatography system according to aspects of the invention. In situ calibration may be achieved by including in the system an on-board supply of a calibration standard in container 166. The calibration standard may be a fluid having known constituents and known quantities of those constituents. The apparatus may be periodically calibrated by injecting a sample of the calibration standard into the column 104 instead of a sample of the formation fluid. Referring to FIG. 4A, a switching valve (not shown) external to the injector 102 may be attached to Port A. Thus, instead of arrow 138 indicating the injection of the sample of formation fluid, the arrow 138 indicates the flow of the calibration standard into Port A. This allows the calibration standard to be injected into the gas chromatography apparatus for calibration proposes. In one embodiment, the calibration standard may contain known concentrations of components that cover the designed analysis range of the column(s) 104. One or more directional valves may be incorporated into the flow channels to allow the flow path to be reversed to back-flush the system with carrier gas before and/or after calibration. As an alternative, a second small sample volume port, similar to Port A, on the rotary injector may allow the calibration standard to be injected into the gas chromatography apparatus without the need to flush the contents of Port A.

As discussed above, some or all of the components making up a gas chromatography apparatus according to embodiments of the invention may be implemented at the microscale. Particularly, referring again to FIGS. 1, 3 and 5, at least some of the injector 102, column(s) 104 and detector(s) 106 may be micro-scale devices and may be coupled to the micro-fluidic platform 108. In addition, as also discussed above, in at least some embodiments, these components may be MEMS devices. An advantage of the geometry of these components is the ability to achieve fluidic connections without the use of standard fluidic connections, such as tubes and fittings. Micro-scale devices lend themselves to near-zero dead volume connections, which may be crucial to the quality of chromatography. Elimination tubes and fittings may also facilitate thermal management as well as elimination of sources of contamination, as discussed further below.

Fluidic interconnections between various components of a gas chromatography apparatus can be significant sources of dead volumes and leakages, which can contaminate the sample. Particularly for chromatography systems which may need to operate in high pressure and temperature environments, these connections can pose significant design challenges. Moreover, even commercially available miniature connectors can add significant thermal mass compared to mass of micro-scale gas chromatography components, which can lead to difficulties in thermal management. As discussed above, the systems proposed by SLS and C2V use glued connections, wherein fused silica capillary tubing is glued into the gas chromatography components. Such connections do not allow part interchangeability and their performance at high temperature and pressure would be questionable. Therefore, according to one embodiment, a gas chromatography system including micro-scale GC components coupled to a micro-fluidic platform may allow reduction or even elimination such complications.

Referring to FIG. 6, there is illustrated one example of a micro-fluidic platform 108 coupled to an injector 102, column 104 and detector 106 disposed in a linear arrangement. The micro-fluidic platform 108 includes micro-channels 156 for the flow paths (indicated by arrows 158) of the fluid sample, carrier gas and waste. The micro-fluidic platform 108 may be constructed by a variety of techniques. For example, SILICON-glass substrates containing micro-channels may be anodically bonded to encapsulated complex fluid circuits that communicate with the GC components. The micro-flow channels may be etched using, for example, lithography-based techniques known in the art. Micro-fabrication techniques may allow positioning of GC components over the micro-fluidic platform with positional variation within a few microns such that the fluidic ports are well aligned while also providing a high degree of surface flatness. Either anodic bonding or "O"-rings can achieve sealing between the GC components and the platform. The assembly as described above, whether bonded or with O-rings, may inherently minimize dead volumes at connections through good alignment and elimination of large fluid connectors. This may result in better quality of GC analyses, since contamination between samples is eliminated.

According to another embodiment, the micro-fluidic platform may be manufactured out of metallic substrates that may be bonded by thermal diffusion. The micro-fluidic pathways within the substrate may be molded or machined by micro-EDM (electric discharge machining) processes. It may be apparent to those skilled in the art that other manufacturing options may also be used to construct the micro-fluidic platform. Thus, the invention is not limited to the specific examples given herein and this disclosure is intended to cover other such manufacturing techniques that may eliminate the use of tubing and related connectors and which achieves a direct flow path through the GC components via a common platform.

Furthermore, it is to be appreciated that a variety of materials may be used to form the micro-fluidic platform 108. In one example, particularly for a high temperature down-hole environment, materials with consistent thermal expansion properties, such as SILICON-glass, may be chosen to prevent structural deterioration over repeated temperature cycles. Materials of construction, such as SILICON-glass, non-reactive metals, etc. may have the added benefit that the chromatographic separation is not affected by local chemical activity, thus avoiding "active spots." In one example, a SILICON-glass platform may be coated with, for example, an elastomer or thermoplastic to facilitate bonding of the GC components to the platform. Another example material that may be used for the platform is INVAR® (generically, FeNi36), an alloy of iron (64%) and nickel (36%) with added carbon and chromium, which has a low and well-controlled coefficient of thermal expansion. INVAR® is not inherently non-reactive; therefore, a platform that includes INVAR® may be coated to make it non-reactive. Any industry-standard coating may be used including, for example, TEFLON® (generic name, Polytetrafluoroethylene (PTFE)) or SILCOAT® (generic name, colloid silver powder).

Figure 7:
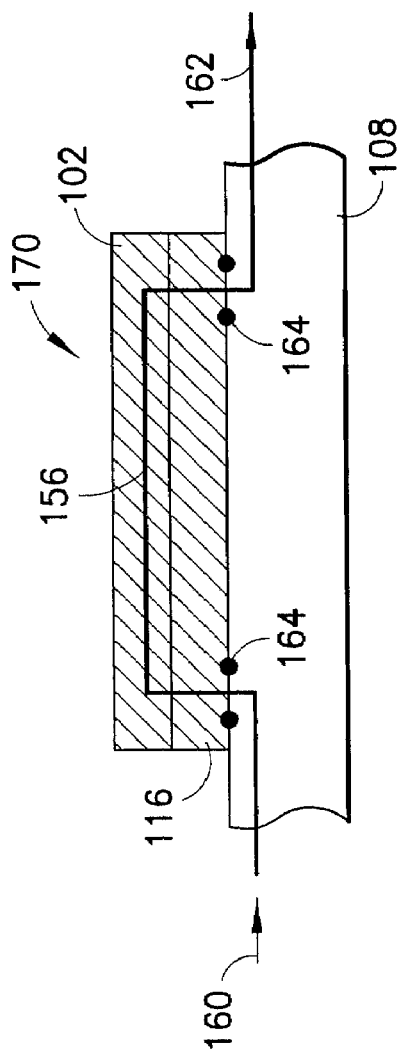
FIG. 7 is an enlarged view of the portion of the gas chromatography apparatus of FIG. 5 enclosed by line 700.

Even a small amount of leakage across fluidic connectors can be detrimental to gas chromatographic analysis. According to aspects of the invention, a micro-fluidic platform may eliminate sources of leakage in several ways. For example, if the GC components are bonded to the platform as discussed above, leakage may be avoided because fluidic connectors may be eliminated. However, in some designs it may not be desirable to have a fully bonded construction for reasons of part interchangeability, replacement, and other practical considerations. Therefore, in another embodiment, "O"-ring seals may be used to connect the flow channels with the various GC components. Referring to FIG. 7, there is illustrated a portion (that surrounded by line 700 in FIG. 5) of the micro-fluidic platform 108 with flow channels 156 coupling to a GC component, for example, the injector 102. "O"-ring seals 164 are illustrated at the junction points between the injector 102 (or heater 116 if present) and the micro-fluidic platform 108.

As discussed above, the sample of formation fluid may be at a pressure much higher than atmospheric. Thus, in for example, the injector arrangement described above with reference to FIGS. 4A and 4B, some of the seals between stages may need to withstand a pressure drop of 20 kpsi or even higher. Referring to FIG. 7, fluid at an input 160 of the injector may be at a first high pressure, P1, and fluid flowing out of the injector (indicated by arrow 162) may be at a much lower pressure, P2, resulting in the above-mentioned pressure drop across at least some of the seals. Conventional rotary valves and other seals have a high potential for developing some leakage, especially at high pressures and temperatures. To mitigate this leakage, the chamber surrounding the components may be filled with an inert gas at a pressure, P3, equal to or higher than the highest expected sample pressure. In one example, this gas may be carrier gas, which may eliminate the need for a separate carrier gas supply container or allow a smaller carrier gas supply container to be used. This can be seen with reference to FIG. 5 in which reference numeral 170 indicates the surrounding carrier gas. With this arrangement, any leakage past the "O"-ring seals (or other seals or valves) would introduce carrier gas into the fluidic path (rather than allowing sample to leak out), which in small proportions does not compromise the chromatographic analyses. In some embodiments, certain components of the gas chromatography system, for example, the sampler 122, may have internal cavities at pressures orders of magnitude different than P3. In such cases, these components (or portions thereof) can be encased in a localized housing having an internal pressure compatible with the device.

A chromatograph generally benefits from precise control and manipulation of the temperature of its major components. As discussed above, in chromatography, separations occur as a sample moves through the column and the time taken for components of the sample to exit the column depends on their affinity to the stationary phase. This affinity has a strong dependence on temperature and therefore, the temperature of the column may need to be very accurately controlled. Some components separate more effectively at low temperatures, whereas other components separate more effectively at high temperatures. Therefore, the temperature of the column may need to be controlled to temperatures below the ambient environmental temperature, particularly for downhole operation where the ambient temperature may be 200 degrees Celsius or higher. Accordingly, a cooling device may be needed to maintain a desired temperature of the column. In addition, some analyses may involve heating the column with a fast and well-defined increasing temperature ramp. After a sample analysis is completed, the column may be cooled to the lower starting temperature. Thus, in some examples, the column may need to be heated and cooled cyclically for each analysis. The rate of heating may need to be fast for certain applications, while the rate of cooling preferably may be as fast as possible to minimize lag time between successive analyses. The cooling process can be particularly time consuming unless a cooling mechanism, such as a fan or other cooling device, is provided. However, both the heating apparatus and the cooling apparatus may contribute to the total thermal mass of the GC device. In general, increasing the thermal mass may make the heating, and particularly the cooling, functions slow and inefficient.

In addition to controlling the temperature of the column, the temperatures of other components, for example, the injector and/or the detector may also need to be controlled. Furthermore, different components may need to be maintained at different operating temperatures from one another. For example, some analyses may require temperature ramping of the column while holding the injector and detector at a constant temperature. Also, the temperature distribution throughout the column, including its inlet and outlet, may preferably be uniform to maintain the quality of chromatographic separation. In many circumstances, the injector and the detector, as well as the fluidic interconnections, may also preferably need to be held at a controlled temperature to avoid cold spots and uneven thermal distribution. In conventional large-scale gas chromatography systems, thermal management is challenging and may be particularly difficult at high ambient temperatures. Traditional heating and cooling devices may have high thermal mass, adding to the complexity of the thermal management. In addition, even "miniaturized" fluidic connections used in traditional gas chromatography apparatus have large enough thermal mass, that thermal management becomes difficult at best. This is particularly the case in a downhole environment where tool space is limited and it is difficult to eject heat from components and cooling apparatus due to the high ambient temperature. Accordingly, using a traditional approach to heating and/or cooling in a downhole tool can result in excessively long analyses times (due to slow, inefficient cooling) along with a complex and inefficient thermal management apparatus.

Figure 8:
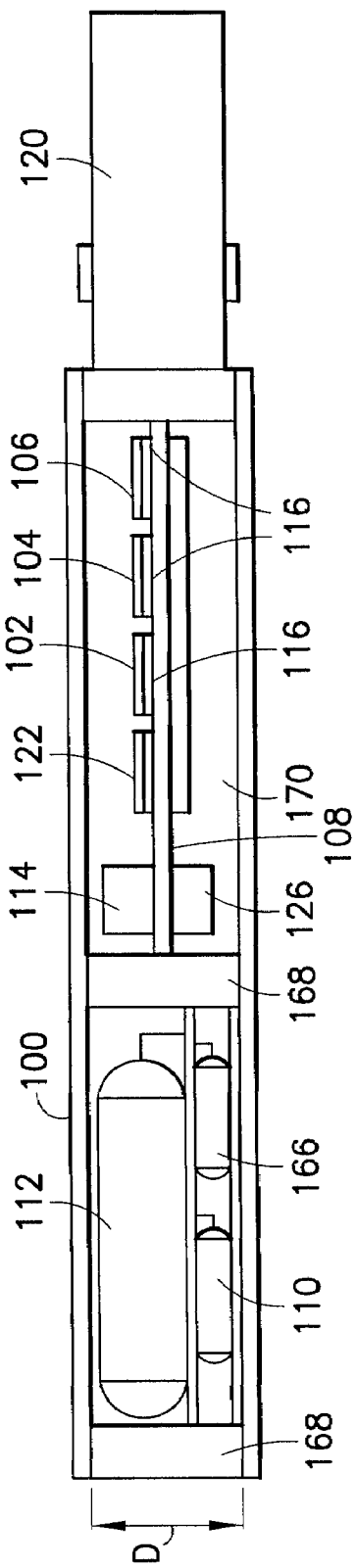
FIG. 8 is a block diagram of another embodiment of a gas chromatography system according to the invention.
Figure 9:
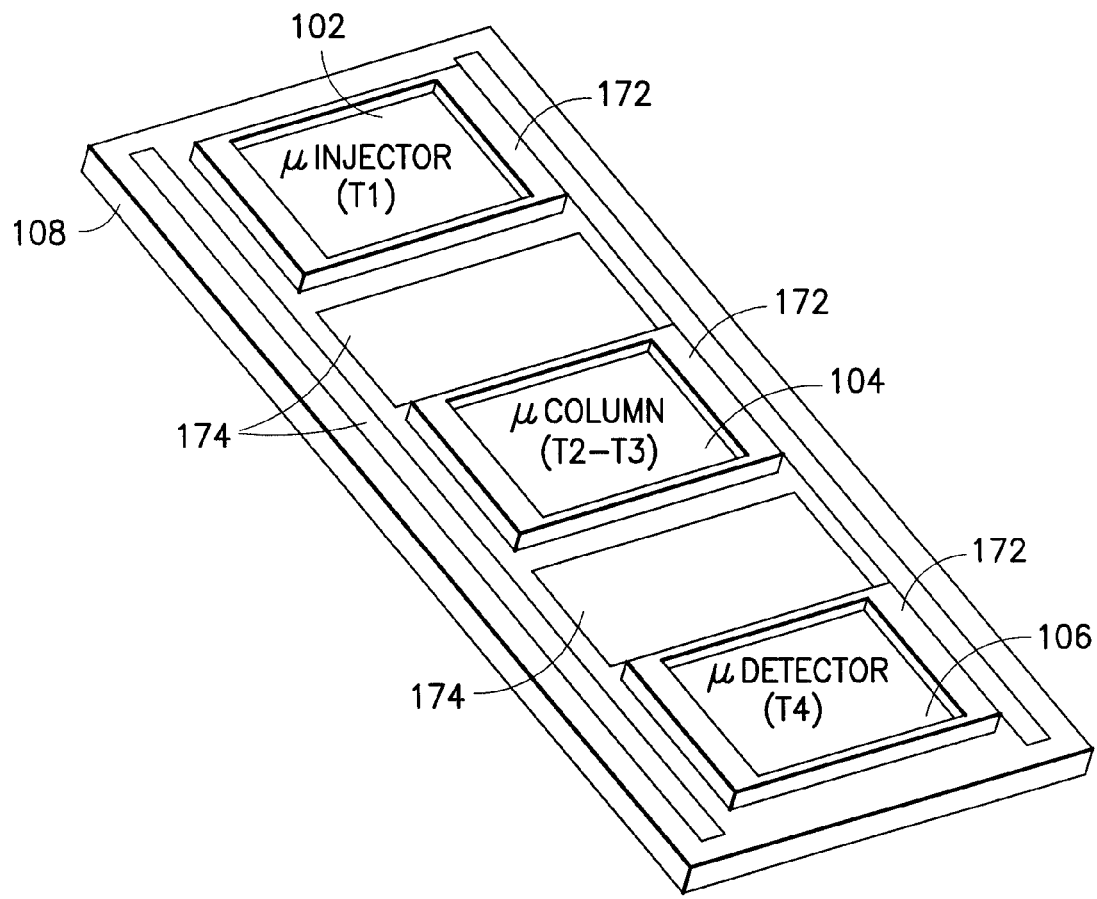
FIG. 9 is a perspective view of components of a gas chromatography apparatus including thermal management components according to an embodiment of the invention.

A micro-scale gas chromatography architecture according to embodiments of the invention may provide major advantages for effective thermal management. For example, the small size of micro-scale components equates to lower thermal mass. This may make temperature control of the components easier because there is a lower mass to be heated and/or cooled. According to one embodiment, the management of temperature transitions between components the injector, column and detector may be controlled by incorporation of thermal stops and traps, as shown in FIG. 9. FIG. 9 illustrates a micro-injector 102, micro-column 104 and micro-detector 106 coupled to the micro-fluidic platform 108 as well as thermal stops 172 and thermal traps 174. A thermal stop is a heated extra mass, sized to preserve the stability of temperature at the perimeter of the heated micro-device. A thermal trap, on the other hand, is a void filled with thermal insulator that limits heat transfer and thus heat loss from the isolated component. Each component may be provided with a heater 116 that may set a desired temperature, or provide a ramped temperature, for each component. Using the thermal stops and thermal traps, the uniformity of temperature within the heated components may be independently preserved. The heaters 116 may be, for example, ceramic heaters or Peltier devices. Peltier devices may be formed as a flat plate that may fit between a GC component and the micro-fluidic platform, as illustrated, for example, in FIGS. 2A-2C. Peltier devices have the property that when electricity is supplied, one side of the device heats up while the other side cools down. Thus, by providing a controlled supply of electricity (using the controls 114 and power supply 126 shown in FIG. 8) to a Peltier device, local heating and/or cooling may be provided for each GC component. For example, the injector may be operated at a first temperature, T1, the column operated over a range of temperatures, T2-T3, and the detector operated at a third temperature, T3. These different temperatures may be maintained at the individual devices by using the heaters 116 together with the thermal traps and stops to isolate the devices from one another. With at least some of the GC components being at the micro-scale, such thermal management may be intrinsically easier to achieve.

Several environments have varying temperatures depending on ambient conditions such as depth underground or underwater. Specifically, the down-hole ambient temperature varies with depth. Therefore, according to another embodiment, a gas chromatography system that may be suitable for down-hole applications, or applications in other non-constant temperature environments, may include additional thermal management features. For example, temperature management of the GC components may be made more efficient by keeping the GC components in a thermally stable environment. To this end, referring again to FIG. 8, the housing 100 may be an isothermic container. For example, the housing 100 may be a tube constructed from Dewar flask-like construction, for example, with mica insulated, layered construction. Such tubes are commercially available, and can optionally be rated to withstand down-hole external pressure. Using such as tube for the housing 100 may facilitate minimization of the heat transfer across the across the housing.

According to another embodiment, within the housing 100, several large thermal masses 168 may be incorporated. These thermal masses may be pre-cooled to stabilize the gas chromatography system at a pre-determined temperature before it is placed in service down-hole. The thermal masses 168 may help to maintain the internal temperature within a certain narrow range, despite changes in the external ambient temperature. In addition, the thermal masses 168 may help to maintain the internal temperature while the temperatures of the various components may be varied as needed to perform the analyses. Provided that the duty cycle of the GC apparatus is limited, these thermal masses may be sized reasonably to fit within a slender cylinder. As discussed above, temperature of individual components of the gas chromatography apparatus may be modulated using heaters 116. In one example, these heaters may be thermo-electric devices (Peltier devices) or ceramic heaters.

Referring again to FIG. 8, a cooling device 120 may be included in the gas chromatography system according to embodiments of the invention. In one example, the cooling device may be capable of operating at temperatures around 200 C and providing a temperature reduction of about 100 C. One example of a suitable cooling device is a Sterling-cycle cooling device. Such a cooling device may provide a temperature delta of about 100 C between "hot" and "cold" ends, both of which can be large thermal masses as discussed above. Using a correctly sized cooling device 120 in conjunction with a Dewar-style enclosure for the housing and thermal masses, an internal environment having an average temperature of less than about 100 C can be created within the housing, despite high external ambient temperature. Such an internal temperature may be conducive to standard chromatographic analytical methods. The above-described arrangement, including the use of thermal masses, thermal traps and thermal stops, together with a cooling device, may be effective due the low thermal mass of micro-scale GC components compared to the rest of thermal management scheme described above.

As discussed above, one GC component that may require or benefit from precisely controlled, flexible thermal management is the gas chromatography column. For example, as discussed above, for some analyses, the column may be provided with a fast temperature ramp and/or may be quickly cooled between analyses to speed up data acquisition time. One example of a GC column according to an embodiment of the invention is a MEMS device that includes a SILICON substrate with a contiguous channel fabricated therein and coated with a desired stationary phase for chromatographic analysis. To achieve thermal management, the column may include integrated heating and/or cooling devices. These devices may control the temperature of the column independent of the surrounding temperature of the overall chromatography system and other GC components within the system.

Referring to FIG. 10, there is illustrated a top view of one example of a geometry for a micro-scale GC column implemented as a microchip and including embedded heating and optional cooling. In the illustrated embodiment, the micro-column includes a SILICON substrate 176. A contiguous column channel 178 is fabricated in the SILICON substrate, for example, by etching or micro-machining, and provides the flow pathway for the sample through the column. The channel is coated with a desired stationary phase. Ports 184 may couple the column channel to, for example, the micro-fluidic platform or to another GC component (e.g., a detector or second column). A second contiguous channel 180 may be fabricated in the substrate 176 interleaved with the column channel 178, as shown in FIG. 10. This channel 180 may contain a heating element (not shown). For example, the heating element may be a resistive wire (e.g., a metallic conductor coated with a dielectric insulator) that is laid inside the channel 180. Alternatively, a conductive (e.g., metallic) layer may be deposited on the channel 180 as well as optionally on other surfaces of the microchip. The heating element (e.g., conductive layer or resistive wire) may be coupled to the power supply 126 (see FIG. 1) such that the heating element may be electrically heated to heat the column.

Referring to FIG. 11, there is illustrated a cross-sectional view of the column of FIG. 10 taken along line 11-11 in FIG. 10. A contiguous cooling channel 182 may be provided on the reverse (with respect to the column channel) of the microchip and thus, can be seen in FIG. 11. In one embodiment, a cooling fluid may be provided in the cooling channel 182, as discussed further below. It is to be appreciated that the representative geometries shown in FIGS. 10 and 11 are for illustration only and are not intended to be limiting. Various other geometries are envisioned and may be apparent to those skilled in the art. For example, the cooling channel may be provided on the same side of the microchip as the column channel. In another example, the heating channel may be provided on the reverse side of the microchip. In another example, either or both of the heating and cooling channels may comprise a plurality of channels, rather than a single contiguous channel. These and other modifications to the geometry that may be apparent to those skilled in the art are intended to be part of this disclosure. Furthermore, although not shown in FIGS. 10 and 11, the GC column may be provided with an optional low thermal mass heating device, such as a thermoelectric heating device as discussed above, in addition to the heating channel 180. In one example, such a heating device may include a low thermal mass thin-film Peltier device that may be attached to one or both sides of the microchip. The thin-film Peltier device may be approximately the same size as the microchip and may be used to provide heating and/or cooling to achieve a desired ambient or in the case of a ramped system, a desired starting temperature for the GC column, as discussed above. Embodiments of the micro-column thus may integrate a heater, an optional flow path for a cooling fluid, and a GC separation column in a MEMS device having very low thermal mass.

To estimate the heat capacity of the micro-column, the following assumptions and constants apply:

The microchip includes a SILICON-glass substrate and has dimensions: 1 cm×2 cm×1 mm (width×length×height).

The density of SILICON is 2.33 grams per cubic centimeter ($g/cm^3$).

The specific heat of SILICON is 0.7 J/gK.

The density and specific heat of glass is assumed to very similar to that of SILICON. As a result of the above assumptions and constants, the heat capacity of the microchip is estimated to be: $K_{chip}=0.33$ J/K. The heat capacity of the microchip is directly dependent on the thermal mass, which is determined by the actual mass and the heat characteristics of the material. The heat capacity of the microchip may determine the power needed to heat the microchip, for example to provide the column with a temperature ramp. For example, with a heat capacity of $K_{chip}=0.33$ J/K, a temperature ramp from 150 C to 350 C in thirty (30) seconds may need a heating power of about 2 W.

Another important metric applying to the micro-column may be cooling power. Cooling power may be defined as the amount of time taken to heat or cool the microchip to a desired temperature for a given applied power. The cooling power may also be affected by the heat capacity of the microchip. The power may be supplied from a source external to the microchip, for example, the power supply 126 (see FIG. 1). Heat may need to be carried away from the solid stationary phase in the GC column. When using a coolant (cooling fluid) in a cooling channel, as discussed above, heat may be transported through the SILICON wall separating the column channel and the cooling channel to the cooling fluid. As a result, the cooling fluid may be heated up and as it flows, may carry the heat away from microchip. Alternatively, rather than supplying a coolant in the cooling channel(s), cooling may be achieved using air convection. The heat from the column may be transported through the SILICON and/or glass substrate to the chip surfaces, then carried away by air convection. For cooling by convection, cooling channels may not be necessary; however, cooling channels may increase the surface area of the microchip, thereby allowing for more efficient convective cooling. The cooling power (or heat sink power), measured in Watts per Kelvin (W/K) may be different for each stage of the heat transfer chain and one or more stages may be a "bottleneck" (i.e., having very low cooling power) in the chain.

For an embodiment of a micro-column as discussed above, estimations of the cooling power of each stage in the heat transfer chain were made for an embodiment using water as a coolant in the cooling channel(s) and for an embodiment using air convection for cooling. The assumptions were:

Thermal conductivity of SILICON: 148 W/m-K (Watts per meter-Kelvin)

Thermal conductivity of glass: 1.05 W/m-K

Thermal conductivity of water: 0.58 W/m-K

For a microchip fabricated on a SILICON-glass substrate, the heat transfer chain may comprise the following stages: conduction in the stationary phase, conduction in the SILICON wall between the column and the cooling channel, and for heat not going into the cooling channels, conduction in the SILICON wafer and conduction in the glass layer (overlaying the SILICON). For the case of cooling through the use of a coolant, the heat transfer chain may further comprise the following stages: conduction in the cooling fluid, and heat sink power by heating up the cooling fluid. For the case of cooling using air convention, the heat transfer chain may further include the following stages: natural convection in air, and heat sink power by heating up the air. The stationary phase in the column may generally be provided as a very thin film coating the column channel. Therefore, conduction in the stationary phase can be assumed to have a very high cooling power and will not be a bottleneck. The heat sink power obtained from heating up the air (for an air-cooled system) is assumed to be negligible as the air temperature is assumed to be constant since the size of the microchip is assumed to be very small compared to the overall size of the chromatography system housing. The following table provides estimations of the cooling power for the other stages of the heat transfer chain. The cooling fluid is assumed to be water.

TABLE 1

| Heat Transfer Stage | Cooling Power (W/K) |
|---|---|
| Conduction in the SILICON wall | 600 |
| Conduction in the cooling fluid | 2.4 |
| Heat sink power by heating up the cooling fluid | 0.002 |
| Conduction in the SILICON wafer | 60 |
| conduction in the glass layer | 0.4 |
| Natural convection in air | 0.004 |

The cooling power of conduction through the SILICON wafer is estimated to be significantly lower than that of conduction through the SILICON wall because the wafer is assumed to be substantially thicker than the wall separating the column channel from the cooling channel. It can be seen from the above estimations that the bottleneck in each case is the convection stage.

The following examples were performed using simulations to verify the above assumptions and to determine an efficient embedded cooling mechanism. In each example, the above-mentioned dimensions for the microchip, as well as the above-mentioned constants for the materials are assumed.

Example 1

In this example, Helium was used as a coolant in the cooling channel 182. The following constants and conditions were used:

Flow-rate of the Helium: 250 cm/sec. (centimeters per second)

Density of Helium: 0.1786 g/L (grams per liter)

Specific heat of Helium: 5.19 J/gK

The cooling channel had a cross-section of 25 micrometers (μm) by 100 μm. With these constants and conditions, the cooling power of the Helium may be calculated to be $P_{He}=5.8\times10^{-6}$ W/K.

Without taking into account the space distribution of the temperature within the GC column, and assuming that the heat transfer between the column and the coolant (being the only heat loss in the column) is instantaneous and complete, the differential equation governing the heat absorption by the coolant inside the cooling channel can be described as:

$$-\frac{dT}{dt} = \frac{P_{cooling}}{K_{chip}}(T - T_{ambient}) \quad (1)$$

where T is $T_{max}$ at t=0 (i.e., the maximum temperature of the column at the time cooling begins). The solution to equation (1) can be obtained:

$$T = T_{ambient} + (T_{max} - T_{ambient})\exp\left(-\frac{P_{cooling}}{K_{chip}}\right) \quad (2)$$

Figure 12:
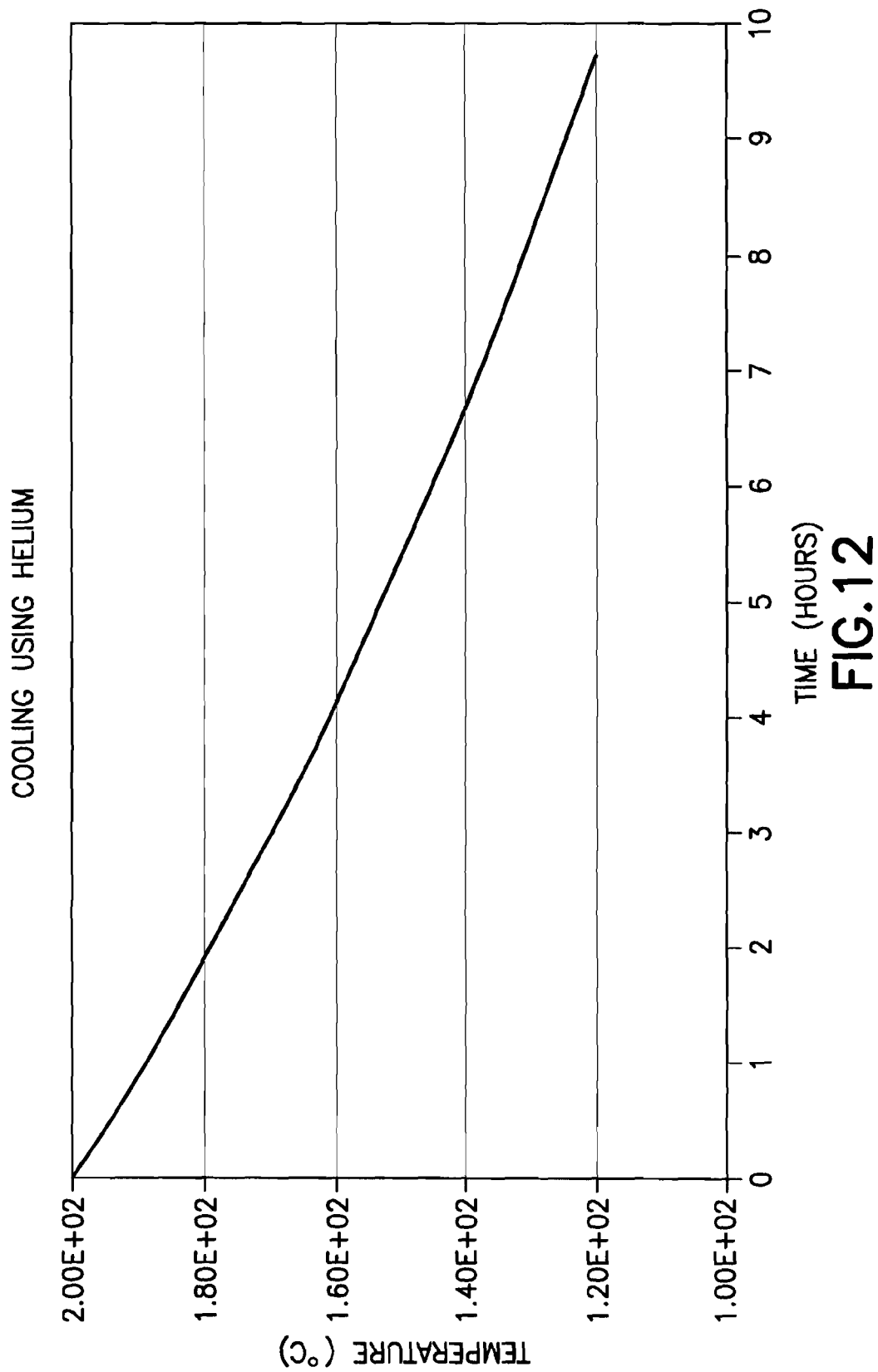
FIG. 12 is a plot of temperature versus time for cooling using Helium.

Referring to FIG. 12, there is illustrated a plot of the temperature T versus time t, using $P_{cooling}=P_{He}$. $T_{max}$ was 200 degrees Celsius (C) and $T_{ambient}$ was 25 C. It can be seen that using Helium as a coolant is not efficient as it took several hours for T to drop from $T_{max}$ to $T_{ambient}$. It is to be appreciated that the ambient temperature may be the natural ambient temperature. Alternatively, if the system is used, for example, in a downhole or other environment having a high natural ambient temperature, the ambient temperature $T_{ambient}$ may be controlled by another heating/cooling device, such as a Peltier thermoelectric device, as discussed above.

Example 2

In this example, water was used as a liquid coolant in the cooling channel 182 of the microchip. The following constants and conditions were used:

Flow rate of the water: 1 μL/sec. (micro-liters per second)
Density of water: 1 kg/L (kilograms per liter)
Specific heat of water: J/gK The cooling channel again had a cross-section of 25 micrometers (μm) by 100 μm. With these constants and conditions, the cooling power of the liquid water may be calculated to be $P_{water} \approx 0.002$ W/K.

Thus, the cooling power of the liquid water was substantially greater than the cooling power of Helium in Example 1. Furthermore, if sufficient heat were imparted to the liquid flowing in the channel to evaporate the liquid, the cooling efficiency would greatly increase due to the latent heat absorption during the phase change from liquid to vapor. Therefore, according to one embodiment, a liquid with an appropriate boiling point can be chosen based on the expected operating temperature of the device such that evaporation may occur to increase cooling efficiency.

Figure 13:
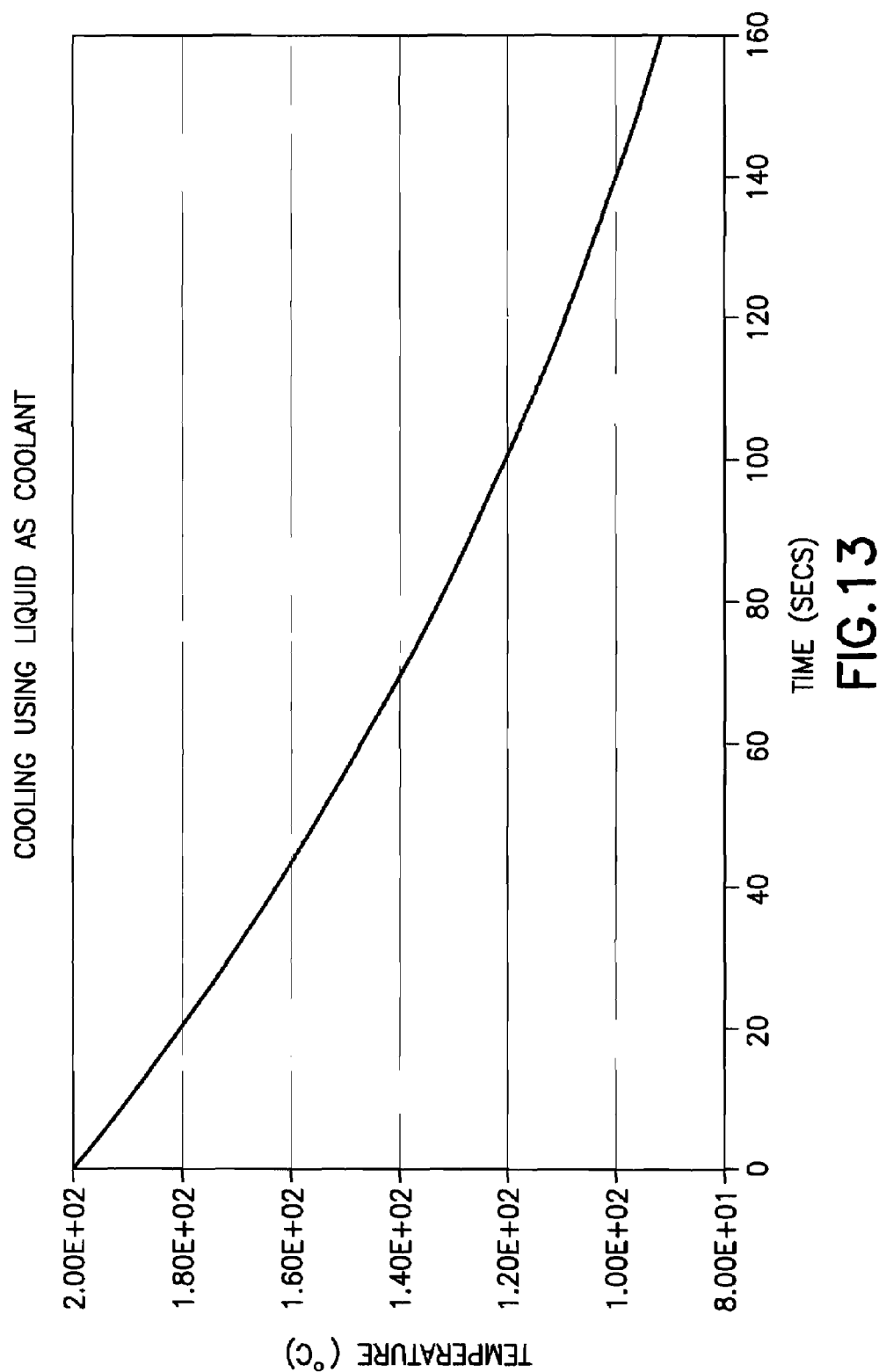
FIG. 13 is a plot of temperature versus time for cooling using a liquid coolant.

Referring to FIG. 13, there is illustrated a plot of the temperature T versus time t, using $P_{cooling}=P_{water}$ in equation (2). $T_{max}$ was again 200 degrees Celsius (C) and $T_{ambient}$ was again 25 C. It can be seen from FIG. 13 that the time taken to cool to the ambient temperature is a few minutes. Thus, this example shows that using water as a coolant is far more efficient than using Helium. In addition, if a liquid (not necessarily water) were chosen such that evaporation may further speed the cooling, as discussed above, the results with a liquid coolant may be even better.

Example 3

In this example, forced air convection was used for cooling. This example used a fan coupled to the GC system power supply to provide the forced air flow. This example also assumes that no cooling channels are provided on the microchip. Therefore, the effective area of cooling is A=2×1 cm×2 cm=4×10$^{-4}$ square meters (m$^2$). The flow rate of the fan was assumed to be 0.87 m/s, giving a forced convection coefficient of $h_{forced}$=27.32 W/m$^2$K. Under these assumptions, the forced convection cooling power is:

$P_{forced-convection}$=0.01 W/K.

Figure 14:
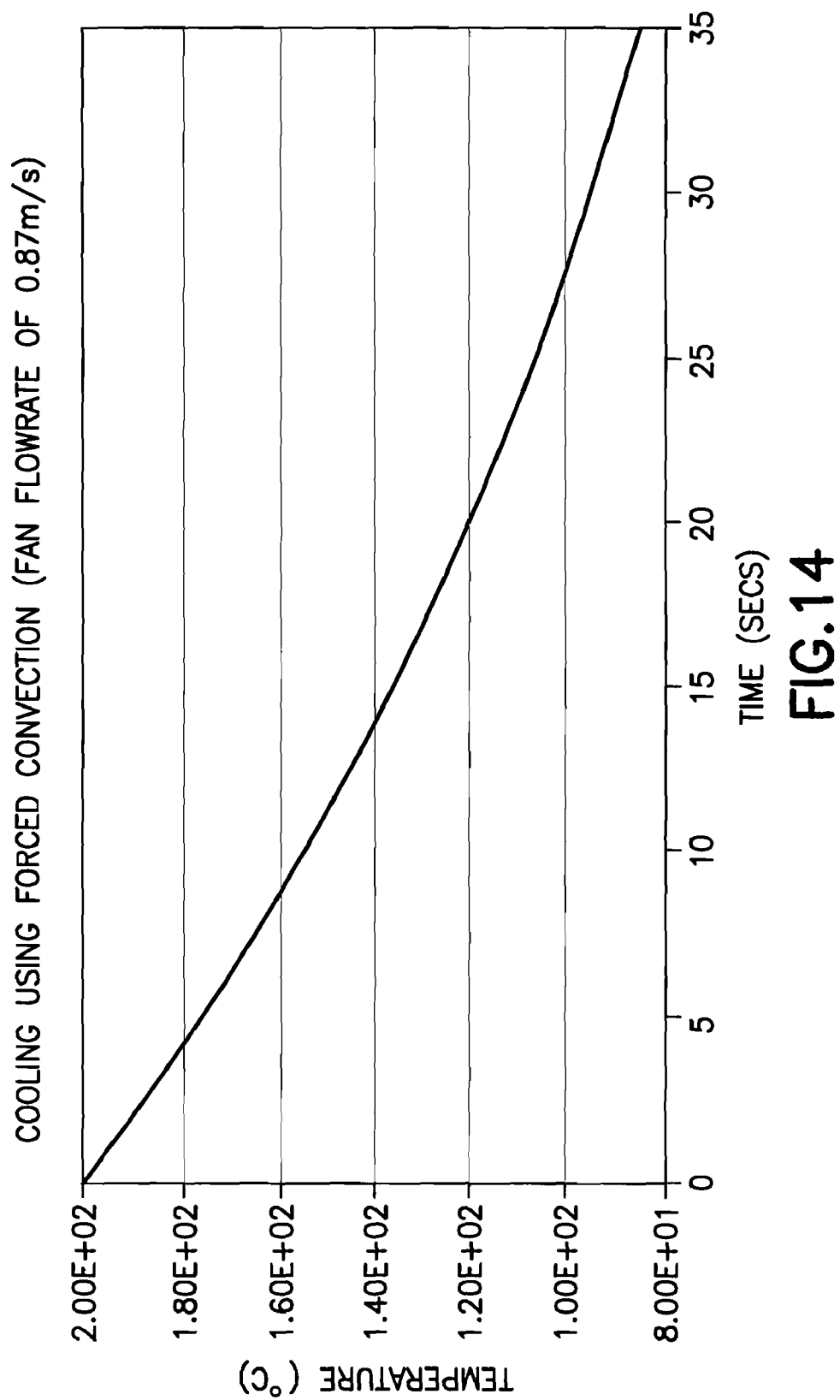
FIG. 14 is a plot of temperature versus time for cooling using forced air convection.

Referring to FIG. 14, there is illustrated a plot of the temperature T versus time t, using $P_{cooling}=P_{forced-convection}$ in equation (2). $T_{max}$ was again 200 degrees Celsius (C) and $T_{ambient}$ was again 25 C. It can be seen from FIG. 14 that the time taken to cool to the ambient temperature is a few seconds. Thus, this example shows that forced convection may be a more efficient cooling mechanism than using a coolant such as Helium or water.

Example 4

In this example, the cooling power of natural (free) air convection is demonstrated. The microchip is again assumed to have no cooling channel and thus the effective area of cooling is A=2×1 cm×2 cm=4×10$^{-4}$ m$^2$. The free convection coefficient is assumed to be $h_{nature} \approx 10$ W/m$^2$K, although this value may differ depending on environmental conditions. With these assumptions, the cooling power of natural convection is:

$P_{free-convection}$=0.004 W/K.

This cooling power is not quite as good as that of forced convection, however, for free convection, no fan is needed which may reduce the power consumption of the system and also reduce system complexity. The cooling power of free convection is also very close to that of a liquid coolant. However, again the design of the microchip and accompanying apparatus using free convection for cooling may be far simpler than for a chip that uses a liquid coolant.

Figure 15:
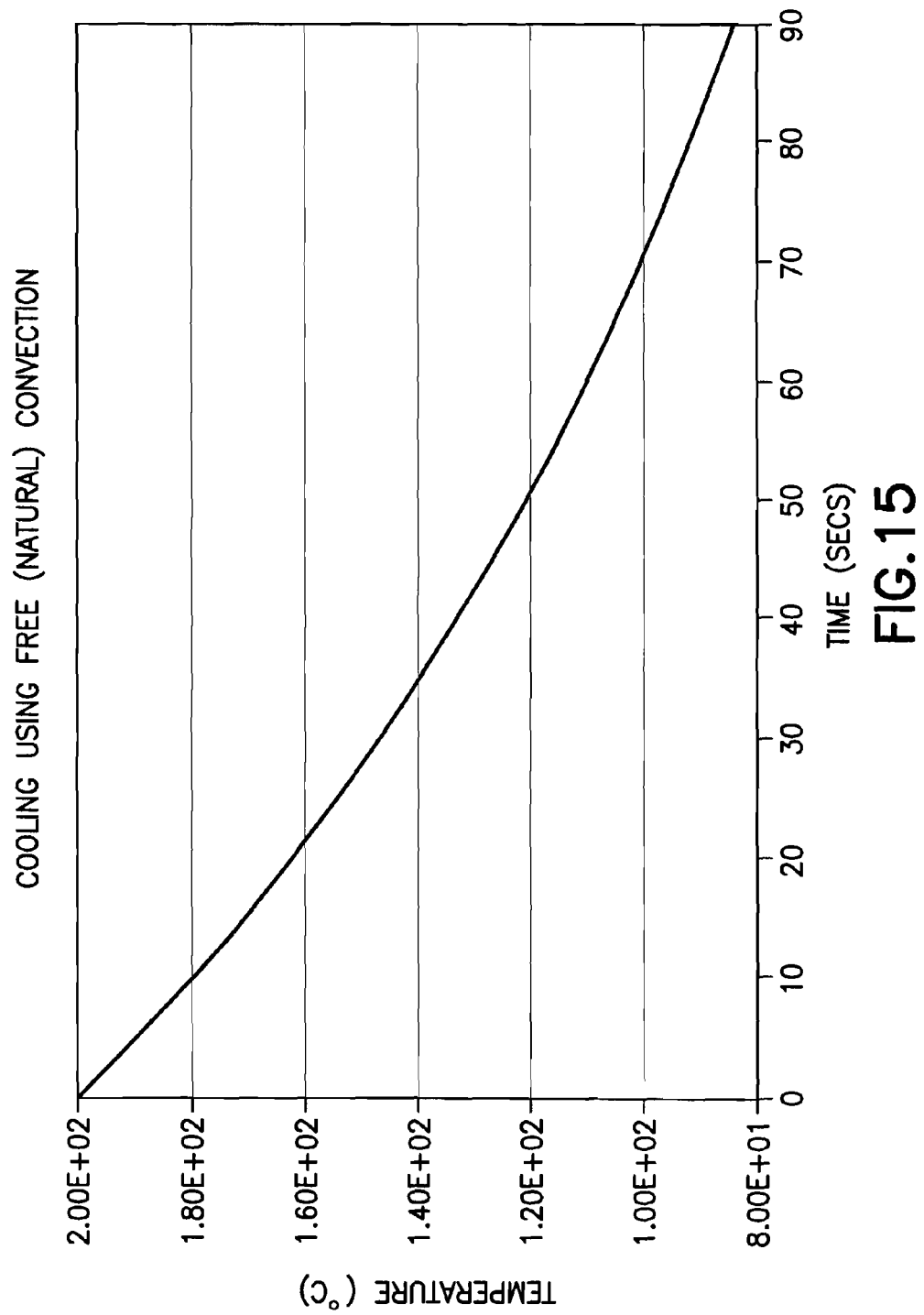
FIG. 15 is a plot of temperature versus time for cooling using natural convection.

Referring to FIG. 15, there is illustrated a plot of the temperature T versus time t, using $P_{cooling}=P_{free-convection}$ in equation (2). $T_{max}$ was again 200 degrees Celsius (C) and $T_{ambient}$ was again 25 C. It can be seen from FIG. 15 that the time taken to cool to the ambient temperature is just over a minute. Thus, this example shows that free convection in air, without the use of a fan, may be sufficient to cool the microchip in a relatively short period of time while providing the added benefit of not requiring any further equipment or electrical power. Furthermore, the value of $P_{free-convection}$ may be improved by including cooling channels in either or both of the top and bottom surfaces of the microchip to increase the effective cooling area of the microchip. For example, including channels 200 μm deep and 1 m long on both sides of the microchip may increase the surface are of the microchip by 200% (assuming microchip dimensions of 2 cm×1 cm, as used above).

Figure 16:
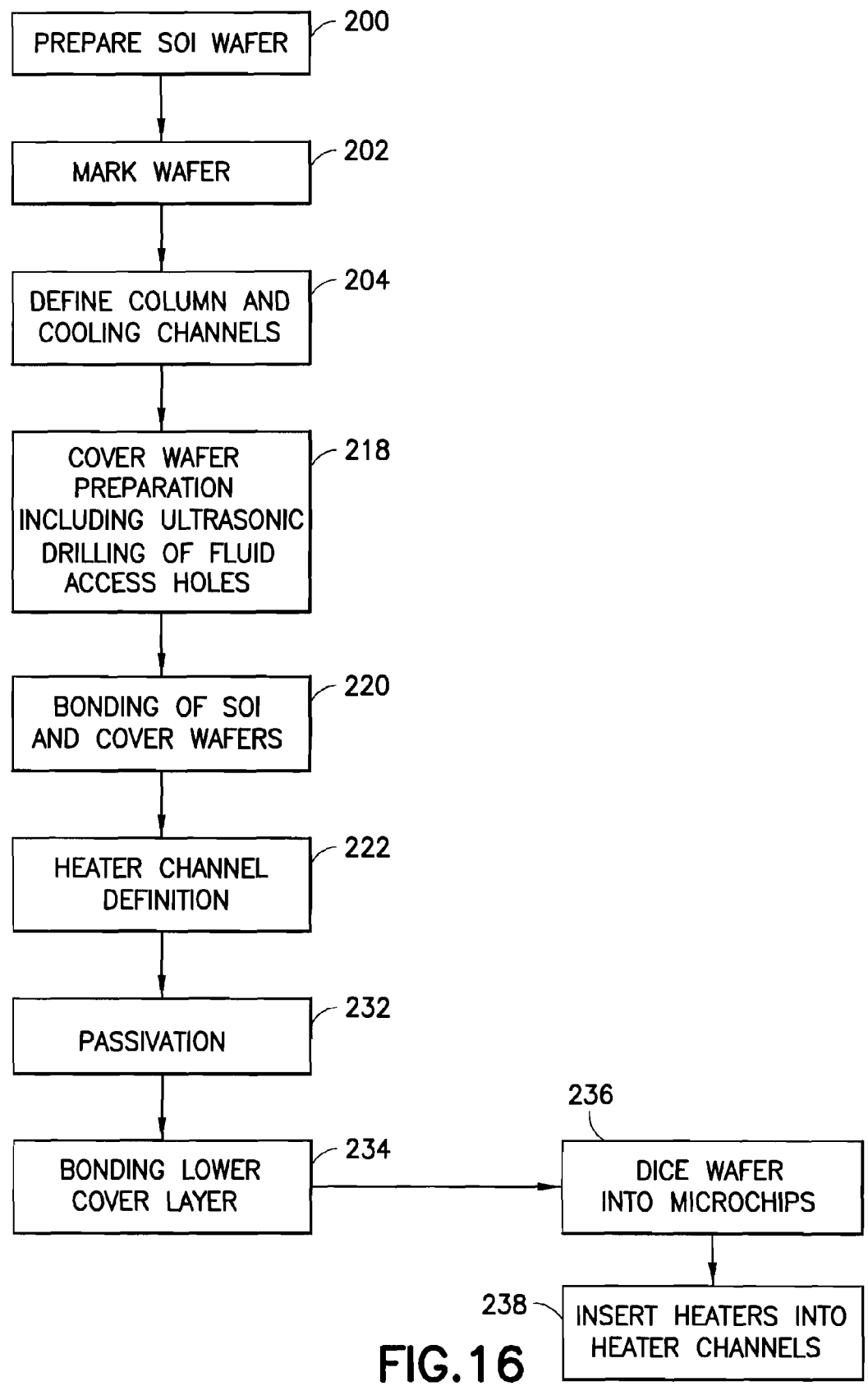
FIG. 16 is a flow diagram illustrating steps of one example of a method of manufacture of a micro-scale gas chromatography column according to an embodiment of the invention.
Figure 17:
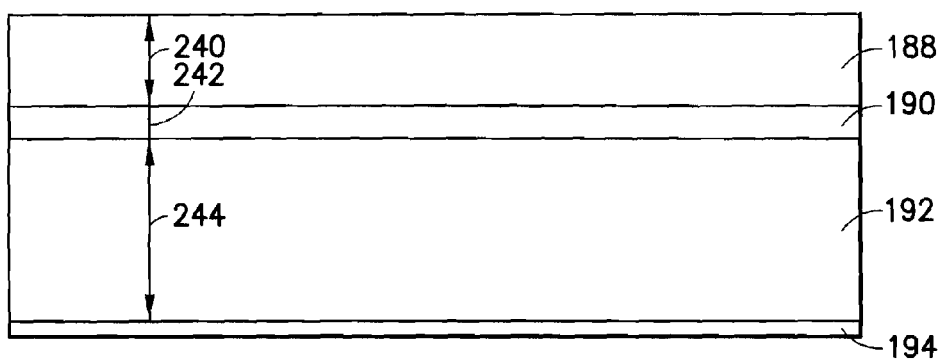
FIG. 17 is a block diagram of one embodiment of a wafer for fabricating a micro-scale gas chromatography column according to aspects of the invention.

As discussed above, a micro-scale GC column including integrated heating and cooling, such as illustrated in FIGS. 10 and 11, may be fabricated on a SILICON-glass, or similar, substrate using micro-fabrication techniques. Referring to FIG. 16, there is illustrated a flow chart for one embodiment of a method of manufacturing a micro-scale GC column. In a first step 200 the wafer may be prepared for the micro-fabrication process. In one embodiment, the wafer may be a SILICON-on-insulator (SOI) wafer and may be approximately four (4) inches in length and width; however, may other dimensions are possible. An example of a wafer is illustrated in FIG. 17. The wafer 186 may comprise a SILICON layer 188 that may have a thickness 240 of approximately 100 μm. Below the SILICON layer 188 may be a buried SILICON-dioxide (SiO$_2$) layer 190. In one example, the buried SiO$_2$ layer may have a thickness 242 of approximately 2 μm. The wafer may further comprise a SILICON substrate 192 that may have a thickness 244 of approximately 450 μm. The backside of the wafer may be polished and include a thin oxide layer 194. It is to be appreciated that the thicknesses for the layers given herein are examples only and are not intended to be limiting. Many other thicknesses of the layers and geometries for the wafer may be apparent to those skilled in the art and are intended to be included in this disclosure.

Referring again to FIG. 16, in a second step 202, the wafer may be marked for later dicing into individual chips. The wafer 186 may be far larger than the individual microchips will be at the end of the manufacturing process. For convenience, however, manufacturing generally takes places at the wafer level to allow multiple chips, sometimes hundreds of chips, to be simultaneously manufactured on one wafer. The wafer is then cut up into the individual chips. Therefore, prior to the bulk of the manufacturing steps, the wafer may be marked such that it is later possible to accurately dice the wafer into the individual chips. In addition, the marking may facilitate accurate alignment of manufacturing tools. This marking procedure may include imprinting a mark layer on or below the surface of SILICON layer 188 using, for example, reactive ion etching.

Figure 19:
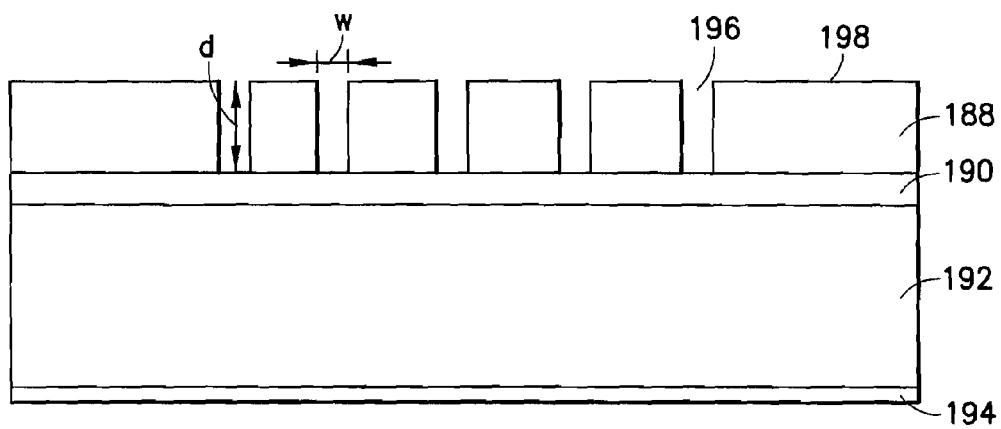
FIG. 19 is a block diagram of one embodiment of a wafer for fabricating a micro-scale gas chromatography column according to aspects of the invention.
Figure 18:
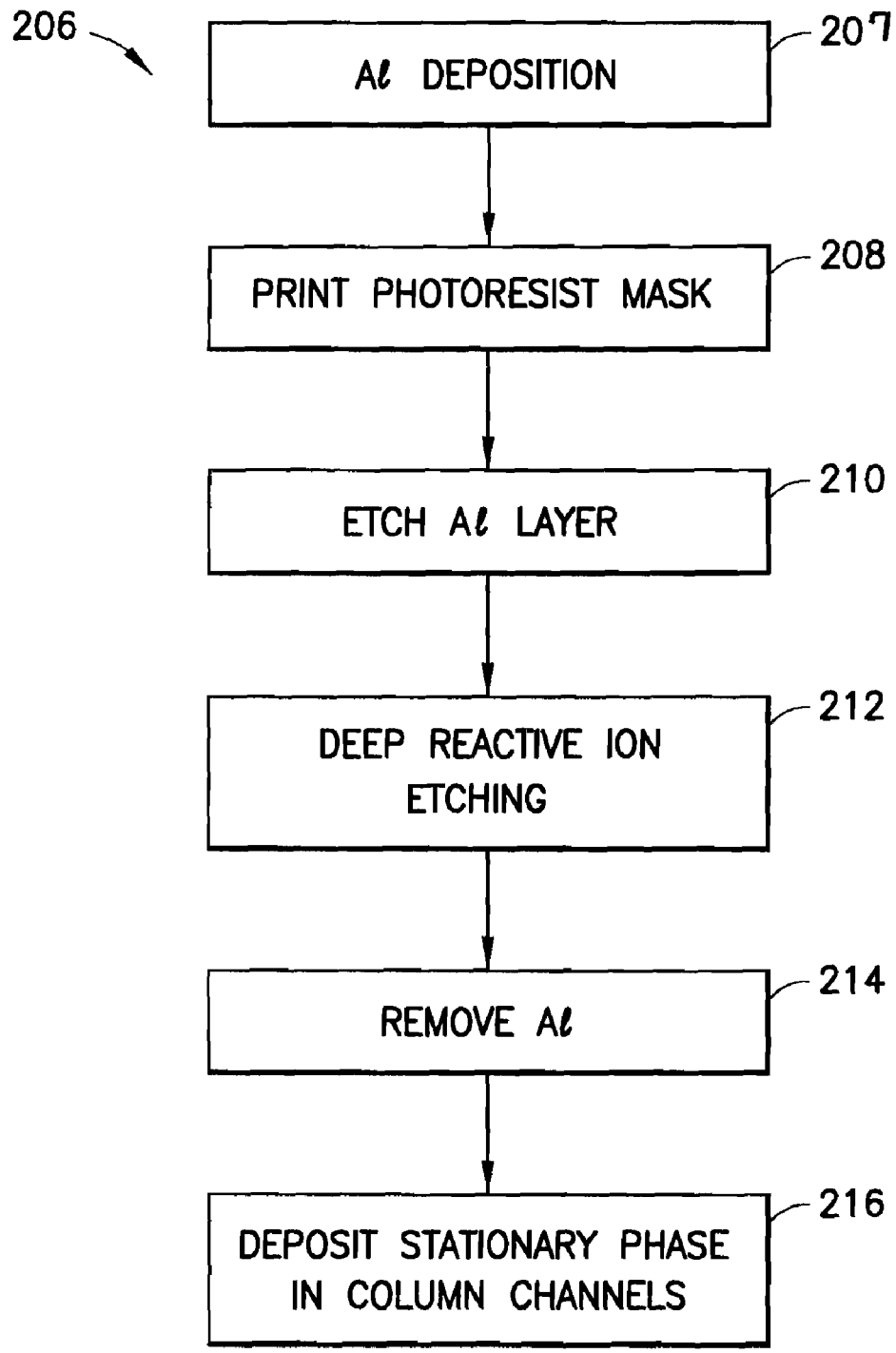
FIG. 18 is a flow diagram illustrating steps of one example of a method of forming channels in a wafer to fabricate a micro-scale gas chromatography column according to an embodiment of the invention.

In a next step 204, channels may be defined on the surface 198 of the SILICON layer 188. As discussed above, in one embodiment the microchip for the GC column may include column channels and cooling channels (which may ultimately have a coolant flowing therein or may simply be to increase the effective cooling area of the microchip) fabricated on the same side of the microchip. Therefore, in one embodiment, step 204 may include fabricating both column and cooling channels. However, in other embodiments the cooling channels may be on the reverse side of the chip, as discussed above, in which case an additional step may be included to form the cooling channels. Channel definition step 204 may include a plurality of process steps. Referring to FIG. 18, there is illustrated a flow diagram of one example of the process steps that may be included to perform the channel definition step 204 (see FIG. 16). First a layer of aluminum may be deposited on the exposed surface of the SILICON layer 188 (step 207). In a next step 208, a photoresist mask may be printed on the aluminum layer to define the channel layout. In a next step 210, the aluminum layer may be etched according to the photoresist mask to begin creating the channels. Next, deep reactive ion etching may be used to etch the channels into the SILICON layer (step 212). In one example, the channels 196 may extend fully through the SILICON layer 188 to the buried SiO$_2$ layer, as shown in FIG. 19. In this example, the channels may have a depth d of about 100 μm. In one example, the channels may have a width w of about 25 μm. However, it is to be appreciated that the invention is not limited to these dimensions. As discussed above, the channels 196 may include, for example, the column channel 178 and cooling channel 182 (see FIG. 11). Once the channels have been etched into the SILICON layer 188, the aluminum may be removed (step 214) and the stationary phase may be deposited on the channels that are to be used as the column channel for each microchip (step 216).

Figure 20:
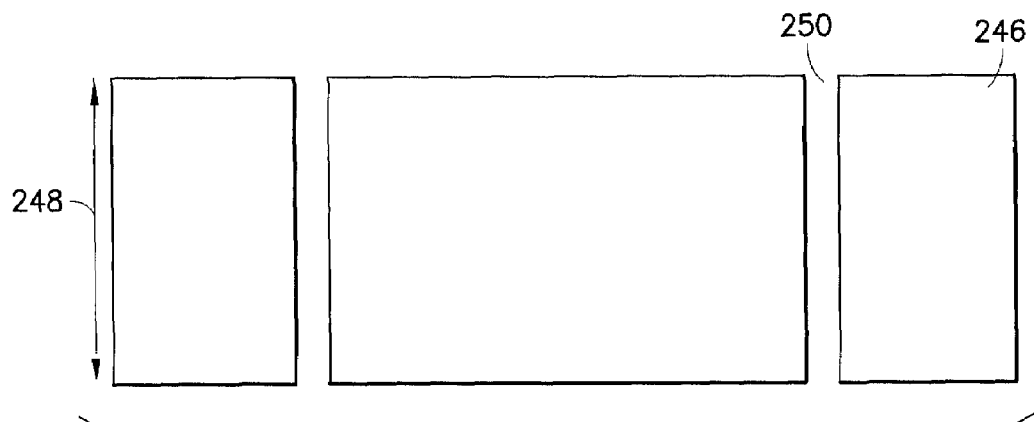
FIG. 20 is a block diagram of one embodiment of a cover layer for the wafer of FIGS. 17 and 19, according to aspects of the invention.

Referring again to FIG. 16, a PYREX wafer may be prepared to form a cover layer for the microchip in step 218. It is to be appreciated that although the PYREX preparation step is illustrated in FIG. 16 as a later step than steps 200-204, the invention is not so limited and the PYREX wafer may be prepared before, during or after the SILICON wafer is prepared and the channels are etched. In one embodiment, the PYREX wafer may be approximately 500 μm in thickness. The PYREX wafer may be bonded to the surface 198 of the SILICON layer of the wafer 186, covering the channels 196. Therefore, preparing the PYREX wafer may include providing fluid access holes in the wafer for the inlets and outlets for both the column channels and cooling channels. These fluid access holes may provide a connection between the column channel and the micro-fluidic platform discussed above. In an embodiment in which a coolant is flowed through the cooling channel, the fluid access holes may also provide a connection between the microchip and a cooling system. In one example, these holes may be formed by ultrasonic drilling. FIG. 20 illustrates one example of a PYREX wafer 246 having a thickness 248 and including the fluid access holes 250. Although it is to be appreciated that a variety of materials may be used for the cover, in at least one embodiment, PYREX may be preferred because it has properties that may facilitate bonding of the cover layer to the SILICON layer. For example, PYREX contains sodium ions which may migrate to the surface of the PYREX wafer and facilitate anodic bonding of the PYREX cover layer to the SILICON layer. Furthermore, PYREX has a coefficient of thermal expansion that is very close to that of SILICON. This may also facilitate good bonding between the cover layer and the SILICON and may minimize, or at least reduce, thermal stresses between the layers when exposed to varying temperatures.

Figure 21:
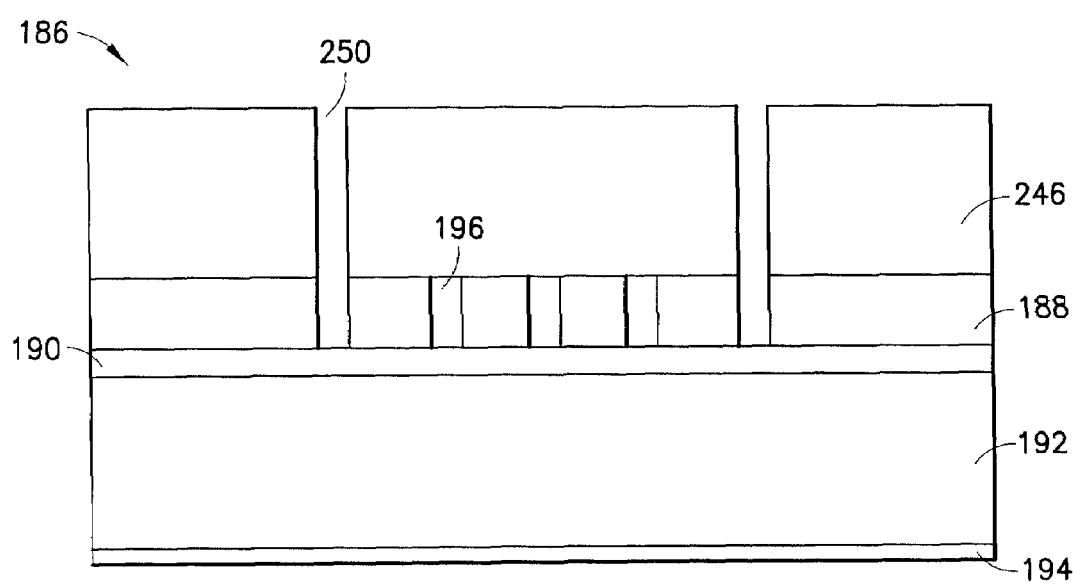
FIG. 21 is a block diagram of one embodiment of a wafer for fabricating a micro-scale gas chromatography column according to aspects of the invention.
Figure 22:
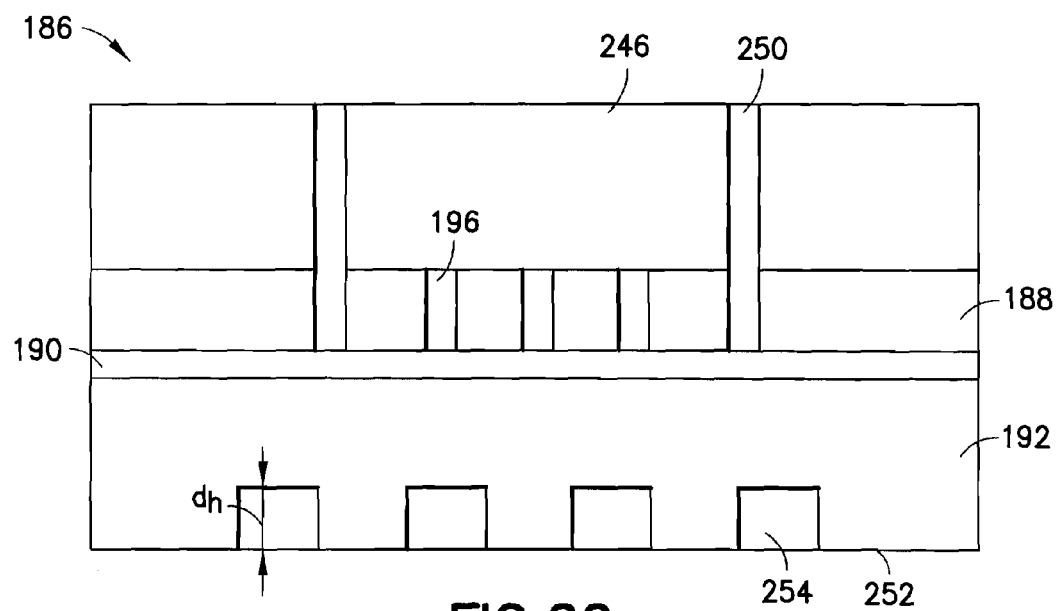
FIG. 22 is a block diagram of another embodiment of a wafer for fabricating a micro-scale gas chromatography column according to aspects of the invention.

Referring again to FIG. 16, in step 220 the cover layer 246 may be bonded (e.g., using anodic bonding) to the surface of the SILICON layer of the microchip. The bonded wafers are illustrated in FIG. 21. The bonding step 220 may include preparing and activating the surfaces of the cover layer and the SILICON layer. Once the wafers are bonded together, the wafers may be cleaned, for example, using standard RCA cleaning. One skilled in the art will recognize that the RCA cleaning method is the industry standard for removing contaminants from wafers. In step 222, heating channels may be defined on the reverse surface 252 of the microchip. Referring to FIG. 22, there is illustrated an embodiment of the microchip including heating channels 254. In this illustration, the heating channels are on the reverse side of the microchip relative to the column channel. However, as discussed above, in other embodiments, the heating channel(s) may be on the same side of the microchip as the column channel. Therefore, the example illustrated in FIG. 22 is not to be construed as limiting. In addition, although the heater channel definition step 222 is illustrated in FIG. 16 as being after the cover bonding step 220, it is to be appreciated that the inventions are not so limited. In other embodiments, the heater channels may be defined prior to preparing and/or bonding of the cover layer to the SILICON layer or may be defined prior to or in conjunction with the column (and cooling) channel definition step 204.

Figure 23:
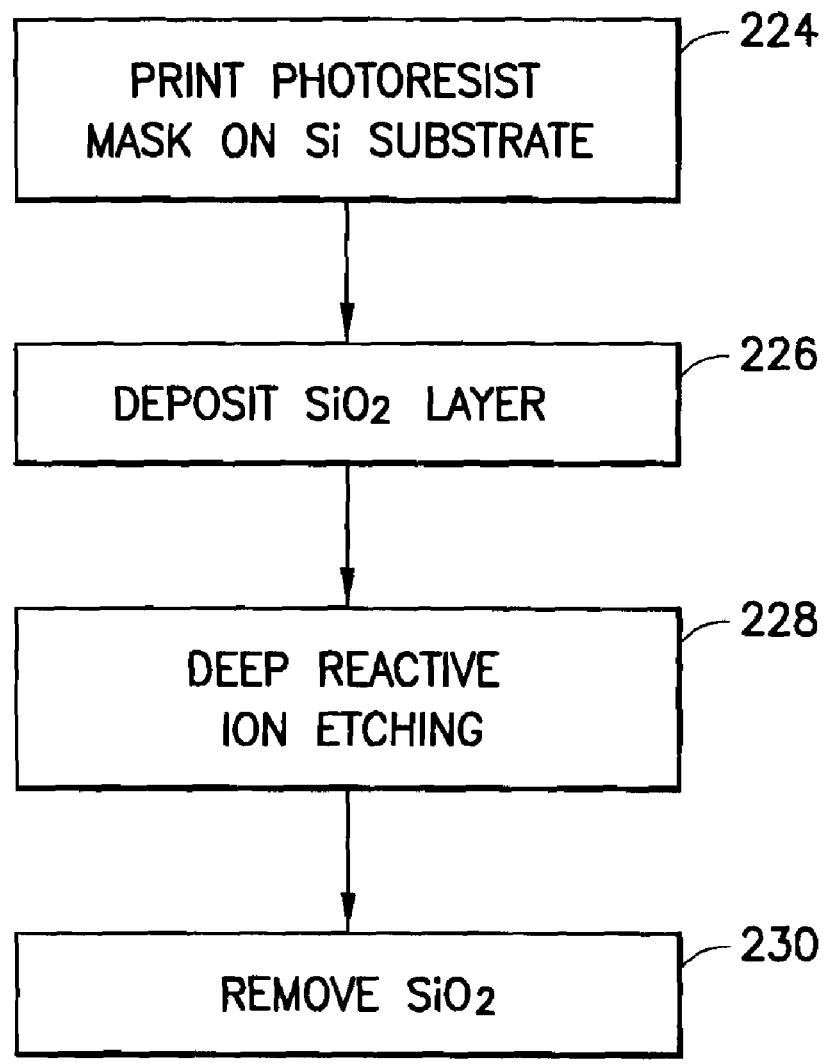
FIG. 23 is a flow diagram illustrating steps of one example of a method of forming channels in a wafer to fabricate a micro-scale gas chromatography column according to an embodiment of the invention.

The heater channel definition step 222 may include a number of process steps. FIG. 23 illustrates a flow diagram of one example of a method of heater channel definition step 222. First, a photoresist mask may be imprinted on the surface 252 of the SILICON substrate 192 to define the layout of the heater channels (step 224). Next, a SiO$_2$ etching layer may be deposited on the masked SILICON substrate (step 226). In a next step 228, deep reactive ion etching may be used to form the heater channels 254 in the SILICON substrate. In one example, the heater channels 254 may have a depth, $d_h$. Once the channels have been formed, the SiO$_2$ deposited in step 226 may be removed (step 230).

Figure 24:
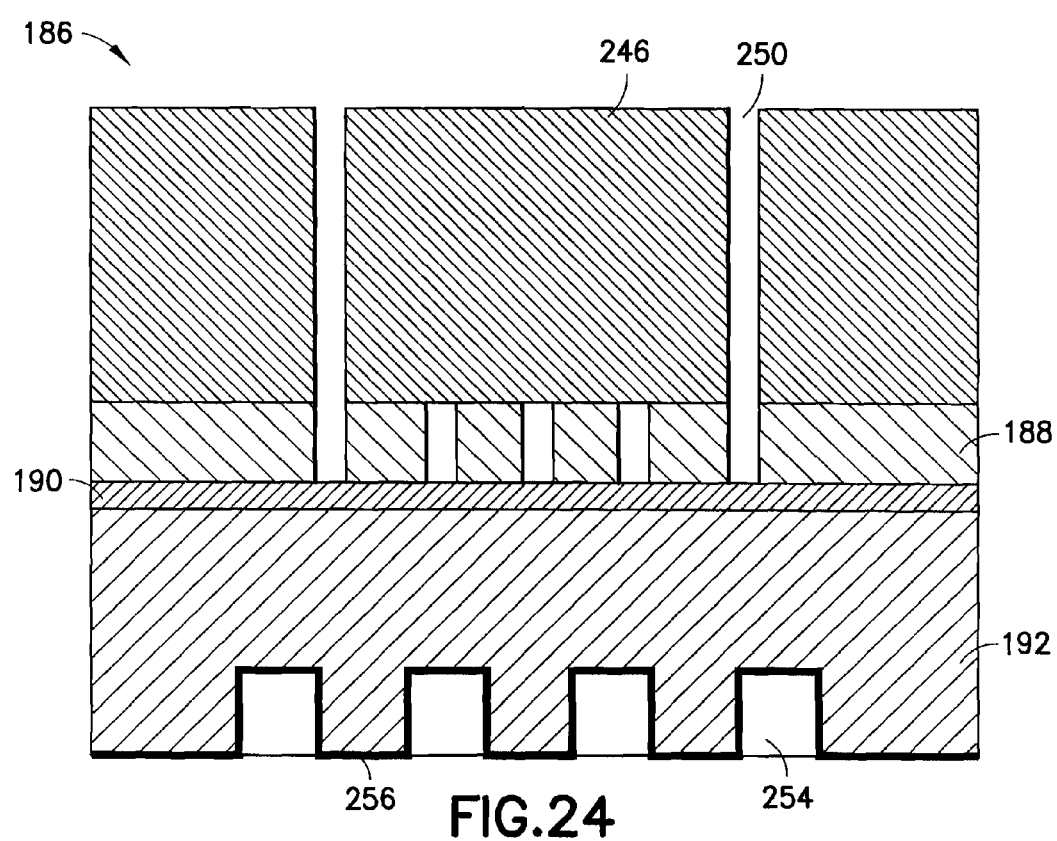
FIG. 24 is a block diagram of another embodiment of a wafer for fabricating a micro-scale gas chromatography column according to aspects of the invention.
Figure 25:
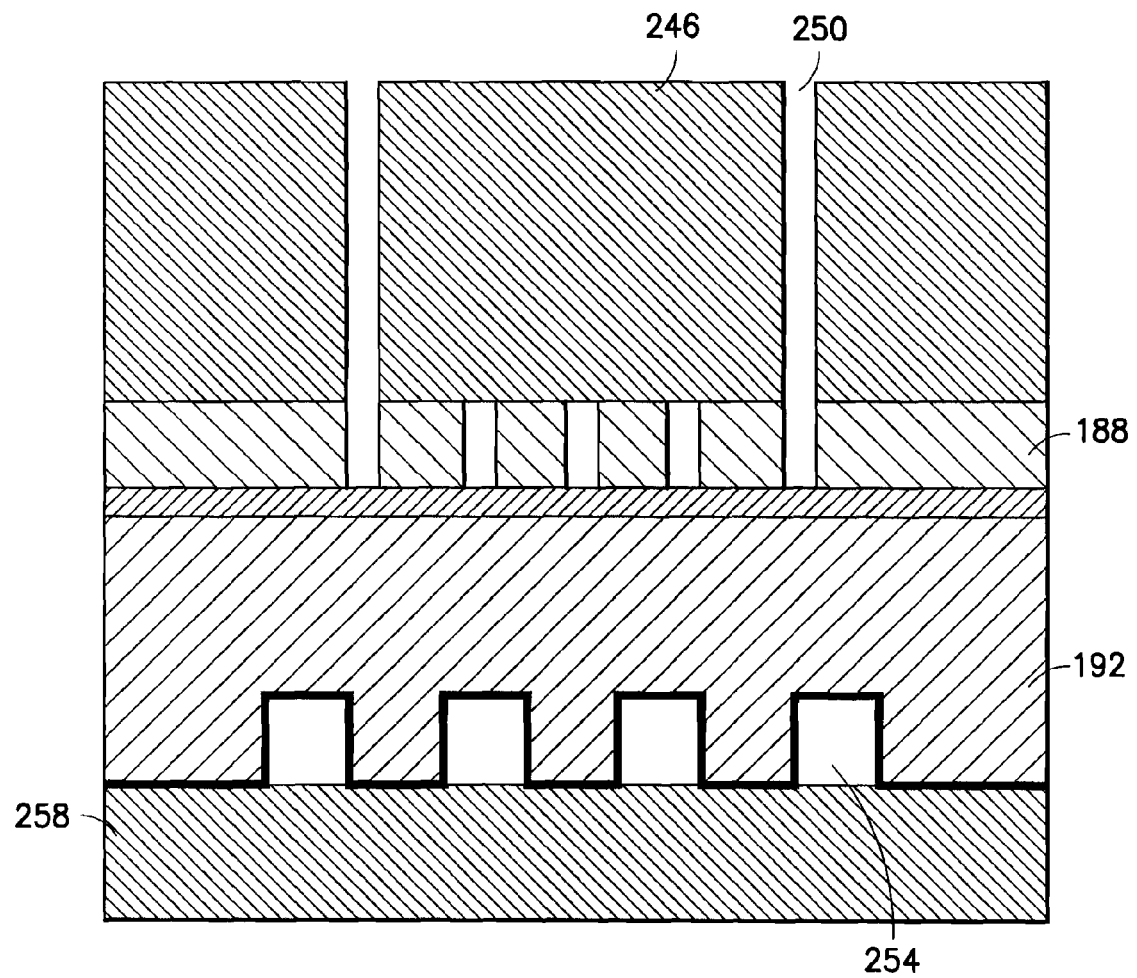
FIG. 25 is a block diagram of another embodiment of a wafer for fabricating a micro-scale gas chromatography column according to aspects of the invention.

Referring again to FIG. 16, after the heater channels have been formed, the wafer may undergo a passivation step 232. Passivation may prepare the surfaces of the microchips to render them substantially chemically inactive. In one example, passivation may include deposition of a wet oxidation layer 256 on the lower surface of the SILICON substrate and on the heater channels 254, as shown in FIG. 24. In one example, the wet oxidation layer may have a thickness of approximately 5000 angstroms (Å). In a next step 234, a second cover layer may be bonded (e.g., using anodic bonding) to the surface of the SILICON substrate, covering the heater channels. An example of the wafer including the second cover layer 258 is illustrated in FIG. 25. In one example, the second cover layer 258 may be a PYREX wafer. As discussed above, PYREX may be preferred for some embodiments because it has a chemistry that is favorable for bonding to SILICON. In one example, the PYREX wafer forming the second cover layer may have a thickness of about 200 μm. Step 234 may also include preparation and cleaning of both the PYREX cover wafer and the SILICON substrate.

Figure 26:
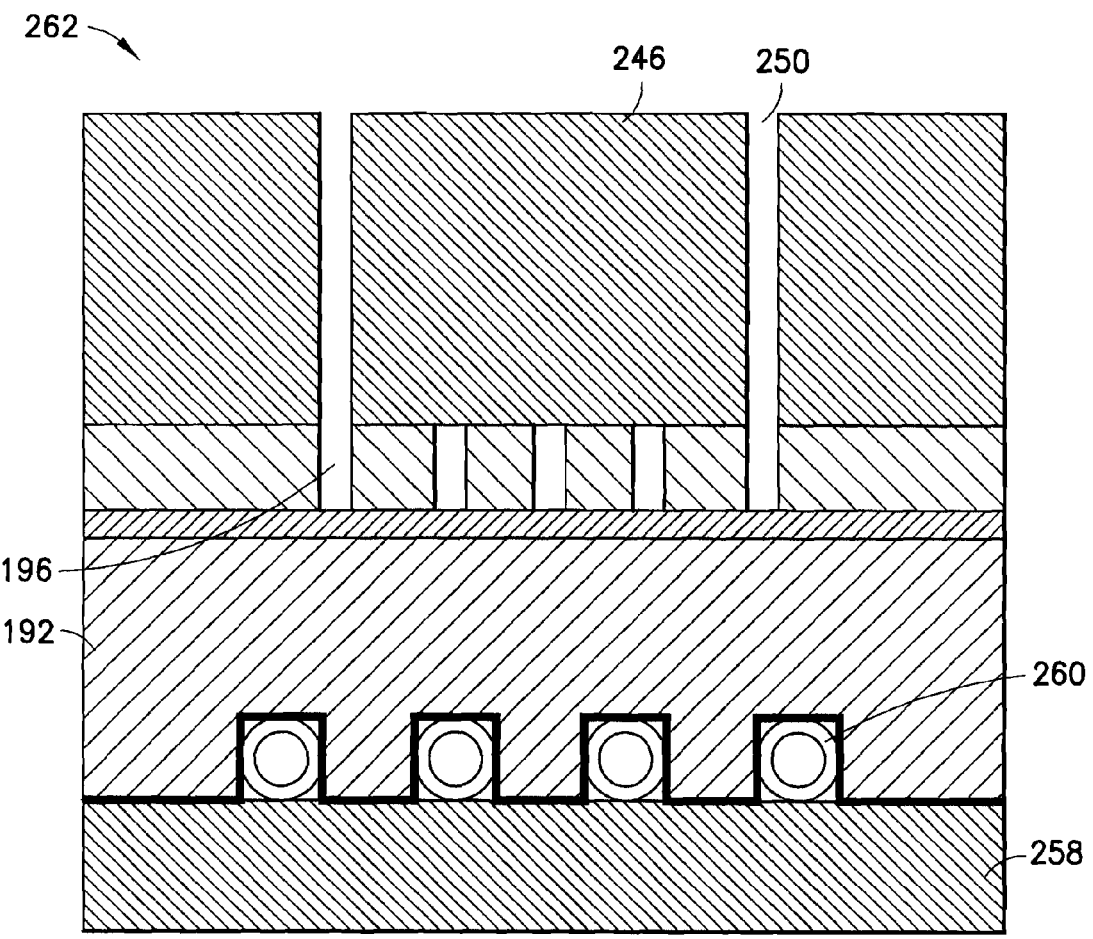
FIG. 26 is a block diagram of another embodiment of a wafer for fabricating a micro-scale gas chromatography column according to aspects of the invention.

Once manufacturing of the microchips on the wafer is complete (i.e., all channels have been formed, surfaces prepared etc.), the wafer may be diced (step 236) into the individual microchips along the dicing marks printed during step 202. In step 238, heaters 260 may be inserted into the heater channels at the diced chip level. However, it is to be appreciated that the heaters may alternatively be inserted into the heater channels at the wafer level, before the wafer is diced into the individual chips. In particular, in embodiments where the heater elements comprise a conductive coating on the surfaces of the heater channels, it may be preferable to deposit the conductive coating at the wafer level rather than at the chip level. Referring to FIG. 26, there is illustrated one embodiment of a microchip 262 that includes a heater 260 disposed in the heater channel. In the illustrated embodiment, the heater is an insulated resistive wire, as discussed above. The microchip 262 provides one embodiment of a micro-scale GC column and the method of manufacturing discussed above is one example of a fabrication method for such a GC column. However, as discussed above, various other geometries are also possible for the micro-scale GC column and it is to be appreciated that the above-described method of manufacturing may be modified to accommodate such other geometries.

In summary, according to various aspects and embodiments of the invention, a gas chromatography system may incorporate a common micro-fluidic platform that interconnects active GC components (e.g., an injector, column(s) and detector(s)) with nearly zero dead volume "tubeless" and "glueless" fluidic connections which reduces or eliminates "active spots," "cold spots" and sources of contamination, all of which would otherwise degrade the quality and/or reliability of measurements. At least some components of the system may be implemented at the micro-scale which, together with micro-flow channels in the fluidic platform, may allow for very low carrier gas consumption. As discussed above, the system may incorporate on-board waste management and carrier gas supply, as well as an on-board power supply (e.g., a battery), as shown in FIG. 8, allowing for self-contained operation. In at least some embodiments, the small size of components may allow the gas chromatography apparatus to be contained in a housing having an inner diameter, D, of about two (2) to three (3) inches, or even less, and a length of between about eight (8) inches and sixteen (16) inches, which is suitable for the geometric limitations of oil and gas wells. In some embodiments the system may incorporate a variety of thermal management components including a housing capable of providing a thermally stable environment, thermal traps and stops to thermally isolate individual components, heating and cooling devices and pre-heated or pre-cooled thermal masses that may provide additional thermal stability.

In addition, components such as the GC column may include embedded heating and/or cooling mechanisms to provide a micro-scale device with integrated thermal management. Such a gas chromatography system may be capable of fast analysis times, for example, approximately one minute or less, due the small sample volume and small flow channels that may be used, as discussed above. In addition, the small thermal mass of micro-scale components may allow fast temperature cycling, allowing for a wait time between analyses of about two (2) minutes or less. Thus, embodiments of the invention may provide a compact, self-contained gas chromatograph having an architecture suitable for down-hole applications as well as applications in many other environments.

It is to be appreciated that the invention is not limited to the specific examples described herein and that the principles of the invention may be applied to a wide variety applications. The above description is therefore by way of example only, and includes any modifications and improvements that may be apparent to one of skill in the art. The scope of the invention should be determined from proper construction of the appended claims and their equivalents.

The invention claimed is:

1. A micro-scale gas chromatography column comprising:
   a substrate;
   at least one contiguous column channel formed in a first surface of the substrate;
   at least one contiguous heater channel formed in the first surface of the substrate, interleaved with the at least one column channel;
   a resistive wire disposed in the at least one contiguous heater channel; and
   at least one contiguous cooling channel formed in a second surface of the substrate.

2. The micro-scale gas chromatography column as claimed in claim 1, wherein the substrate is a silicon-glass substrate.

3. The micro-scale gas chromatography column as claimed in claim 1, further comprising a stationary phase deposited on a surface of the at least one contiguous column channel.

4. The micro-scale gas chromatography apparatus as claimed in claim 1, wherein the micro-scale gas chromatography column further includes a power supply that supplies electrical power and a heating element that is disposed in the at least one contiguous heater channel and coupled to the power supply such that the heating element includes the resistive wire.

5. The micro-scale gas chromatography apparatus as claimed in claim 4, wherein the heating element includes a conductive coating disposed on a surface of the at least one contiguous heater channel.

6. The micro-scale gas chromatography apparatus as claimed in claim 4, wherein the micro-scale gas chromatography column further includes the at least one contiguous cooling channel formed in a second surface of the substrate, the second surface being opposite the first surface.

7. The micro-scale gas chromatography apparatus as claimed in claim 6, further comprising a cooling system including a coolant; wherein the cooling system is coupled to the at least one contiguous cooling channel such that the coolant flows in the at least one contiguous cooling channel.

8. The micro-scale gas chromatography apparatus as claimed in claim 7, wherein the coolant is a liquid.

9. The micro-scale gas chromatography apparatus as claimed in claim 4, wherein one of the at least one contiguous heater channel, the at least one contiguous cooling channel or both is formed in a portion of the second surface of the substrate, the second surface being opposite the first surface.

10. The micro-scale gas chromatography apparatus as claimed in claim 9, wherein the micro-scale gas chromatography column further comprises one of the at least one contiguous cooling channel, the at least one contiguous heater channel or both is formed in a portion of the first surface of the substrate.

11. A gas chromatography apparatus comprising:
a micro-scale gas chromatography column including a substrate having a column channel formed in a first surface of the substrate wherein at least a portion of the column channel includes a resistive wire disposed therein, the column channel having an inlet port and an outlet port, and a surface of the column channel being coated with a stationary phase; and
a micro-fluidic platform coupled to the inlet port and to the outlet port of the column channel.

12. The gas chromatography apparatus as claimed in claim 11, wherein the micro-scale gas chromatography column is anodically bonded to the micro-fluidic platform.

13. A method of manufacture of a micro-scale gas chromatography column, the method comprising:
defining a plurality of column channels on a silicon-on-insulator (SOI) wafer;
defining a plurality of cooling channels on the SOI wafer;
defining a plurality of heater channels on the SOI wafer;
rendering the wafer substantially chemically inactive; and
dicing the wafer into a plurality of microchips, each microchip corresponding to a micro-scale gas chromatography column.

14. The method as claimed in claim 13, wherein the SOI wafer comprises a silicon layer, a silicon substrate, and a buried silicon dioxide layer sandwiched between the silicon layer and the silicon substrate, and wherein defining the plurality of column channels and defining the plurality of cooling channels include forming the column channels and the cooling channels in the silicon layer by deep reactive ion etching.

15. The method as claimed in claim 14, wherein defining the plurality of heater channels includes forming the heater channels in the silicon substrate by deep reactive ion etching.

16. The method as claimed in claim 15, further comprising preparing a borosilicate glass cover layer and bonding the borosilicate glass cover layer to a surface of the silicon layer, such that the borosilicate glass cover layer covers the plurality of column channels and the plurality of cooling channels.

17. The method as claimed in claim 16, wherein the each column channel of the plurality of column channels includes an inlet port and an outlet port; wherein preparing the borosilicate glass cover layer includes ultrasonically drilling fluid access holes through the borosilicate glass cover layer; and wherein bonding the borosilicate glass cover layer to the silicon layer includes aligning the borosilicate glass cover layer with the silicon layer such that the fluid access holes align with the inlet ports and outlet ports of the plurality of column channels.

18. The method as claimed in claim 16, further comprising disposing a heating element in each heater channel of the plurality of heater channels.

19. The method as claimed in claim 18, further comprising bonding a second borosilicate glass cover layer to a surface of the silicon substrate such that the second borosilicate glass cover layer covers the plurality of heater channels.

* * * * *